(12) United States Patent
Pratt et al.

(10) Patent No.: US 11,096,830 B2
(45) Date of Patent: Aug. 24, 2021

(54) DRESSING WITH INCREASED APPOSITION FORCE

(71) Applicant: KCI Licensing, Inc., San Antonio, TX (US)

(72) Inventors: Benjamin Andrew Pratt, Poole (GB); Christopher Brian Locke, Bournemouth (GB); Timothy Mark Robinson, Shillingstone (GB)

(73) Assignee: KCI Licensing, Inc., San Antonio, TX (US)

(*) Notice: Subject to any disclaimer, the term of this patent is extended or adjusted under 35 U.S.C. 154(b) by 590 days.

(21) Appl. No.: 15/755,498

(22) PCT Filed: Aug. 17, 2016

(86) PCT No.: PCT/US2016/047351
§ 371 (c)(1),
(2) Date: Feb. 26, 2018

(87) PCT Pub. No.: WO2017/040045
PCT Pub. Date: Mar. 9, 2017

(65) Prior Publication Data
US 2018/0214313 A1    Aug. 2, 2018

Related U.S. Application Data

(60) Provisional application No. 62/212,787, filed on Sep. 1, 2015.

(51) Int. Cl.
*A61F 13/00* (2006.01)
*A61F 13/02* (2006.01)

(52) U.S. Cl.
CPC .. *A61F 13/00068* (2013.01); *A61F 13/00029* (2013.01); *A61F 13/0216* (2013.01)

(58) Field of Classification Search
CPC combination set(s) only.
See application file for complete search history.

(56) References Cited

U.S. PATENT DOCUMENTS

| 1,355,846 A | 10/1920 | Rannells |
| 1,944,834 A | 1/1934 | Bennett |

(Continued)

FOREIGN PATENT DOCUMENTS

| AU | 550575 B2 | 3/1986 |
| AU | 745271 B2 | 3/2002 |

(Continued)

OTHER PUBLICATIONS

Australian Office Action for related application 2018278874, dated Feb. 12, 2020.

(Continued)

*Primary Examiner* — Guy K Townsend

(57) ABSTRACT

In some embodiments, a dressing assembly may include a dressing bolster, an interface seal, and a base layer. The dressing bolster may include a first side, a second side, and a periphery. The interface seal may be coupled at the periphery of the dressing bolster. The base layer may include a base layer flange configured to be coupled to the dressing and to extend beyond the periphery of the dressing bolster. The dressing assembly may be suitable for treating a tissue site with reduced pressure and for creating an apposition force between a first portion of the tissue site and a second portion of the tissue site. Other systems, apparatus, and methods are disclosed.

24 Claims, 9 Drawing Sheets

(56) References Cited

U.S. PATENT DOCUMENTS

| | | | |
|---|---|---|---|
| 2,547,758 | A | 4/1951 | Keeling |
| 2,552,664 | A | 5/1951 | Burdine |
| 2,632,443 | A * | 3/1953 | Lesher .............. A61F 13/00021 128/888 |
| 2,682,873 | A * | 7/1954 | Everett ............. A61F 13/00029 602/42 |
| 2,860,081 | A | 11/1958 | Eiken |
| 2,910,763 | A | 11/1959 | Lauterbach |
| 2,969,057 | A | 1/1961 | Simmons |
| 3,066,672 | A | 12/1962 | Crosby, Jr. et al. |
| 3,172,808 | A | 3/1965 | Baumann et al. |
| 3,183,116 | A | 5/1965 | Schaar |
| 3,367,332 | A | 2/1968 | Groves |
| 3,376,868 | A | 4/1968 | Mondiadis |
| 3,520,300 | A | 7/1970 | Flower, Jr. |
| 3,568,675 | A | 3/1971 | Harvey |
| 3,648,692 | A | 3/1972 | Wheeler |
| 3,682,180 | A | 8/1972 | McFarlane |
| 3,742,952 | A | 7/1973 | Magers et al. |
| 3,774,611 | A | 11/1973 | Tussey et al. |
| 3,777,016 | A | 12/1973 | Gilbert |
| 3,779,243 | A | 12/1973 | Tussey et al. |
| 3,826,254 | A | 7/1974 | Mellor |
| 3,852,823 | A | 12/1974 | Jones |
| 3,903,882 | A | 9/1975 | Augurt |
| 3,967,624 | A | 7/1976 | Milnamow |
| 3,983,297 | A | 9/1976 | Ono et al. |
| 4,060,081 | A | 11/1977 | Yannas et al. |
| 4,080,970 | A | 3/1978 | Miller |
| 4,096,853 | A | 6/1978 | Weigand |
| 4,139,004 | A | 2/1979 | Gonzalez, Jr. |
| 4,141,361 | A | 2/1979 | Snyder |
| 4,163,822 | A | 8/1979 | Walter |
| 4,165,748 | A | 8/1979 | Johnson |
| 4,174,664 | A | 11/1979 | Arnott et al. |
| 4,184,510 | A | 1/1980 | Murry et al. |
| 4,233,969 | A | 11/1980 | Lock et al. |
| 4,245,630 | A | 1/1981 | Lloyd et al. |
| 4,256,109 | A | 3/1981 | Nichols |
| 4,261,363 | A | 4/1981 | Russo |
| 4,275,721 | A | 6/1981 | Olson |
| 4,284,079 | A | 8/1981 | Adair |
| 4,297,995 | A | 11/1981 | Golub |
| 4,323,069 | A | 4/1982 | Ahr et al. |
| 4,333,468 | A | 6/1982 | Geist |
| 4,343,848 | A | 8/1982 | Leonard, Jr. |
| 4,360,015 | A | 11/1982 | Mayer |
| 4,373,519 | A | 2/1983 | Errede et al. |
| 4,382,441 | A | 5/1983 | Svedman |
| 4,392,853 | A | 7/1983 | Mute |
| 4,392,858 | A | 7/1983 | George et al. |
| 4,414,970 | A | 11/1983 | Berry |
| 4,419,097 | A | 12/1983 | Rowland |
| 4,465,485 | A | 8/1984 | Kashmer et al. |
| 4,475,909 | A | 10/1984 | Eisenberg |
| 4,480,638 | A | 11/1984 | Schmid |
| 4,525,166 | A | 6/1985 | Leclerc |
| 4,525,374 | A | 6/1985 | Vaillancourt |
| 4,529,402 | A | 7/1985 | Weilbacher et al. |
| 4,540,412 | A | 9/1985 | Van Overloop |
| 4,543,100 | A | 9/1985 | Brodsky |
| 4,548,202 | A | 10/1985 | Duncan |
| 4,551,139 | A | 11/1985 | Plaas et al. |
| 4,569,348 | A | 2/1986 | Hasslinger |
| 4,600,146 | A | 7/1986 | Ohno |
| 4,605,399 | A | 8/1986 | Weston et al. |
| 4,608,041 | A | 8/1986 | Nielsen |
| 4,617,021 | A | 10/1986 | Leuprecht |
| 4,640,688 | A | 2/1987 | Hauser |
| 4,655,754 | A | 4/1987 | Richmond et al. |
| 4,664,652 | A | 5/1987 | Weilbacher |
| 4,664,662 | A | 5/1987 | Webster |
| 4,705,543 | A | 11/1987 | Kertzman |
| 4,710,165 | A | 12/1987 | McNeil et al. |
| 4,715,857 | A | 12/1987 | Juhasz et al. |
| 4,733,659 | A | 3/1988 | Edenbaum et al. |
| 4,743,232 | A | 5/1988 | Kruger |
| 4,753,230 | A | 6/1988 | Carus et al. |
| 4,753,232 | A | 6/1988 | Ward |
| 4,758,220 | A | 7/1988 | Sundblom et al. |
| 4,787,888 | A * | 11/1988 | Fox .................... A61K 41/0047 601/2 |
| 4,826,494 | A | 5/1989 | Richmond et al. |
| 4,832,008 | A | 5/1989 | Gilman |
| 4,838,883 | A | 6/1989 | Matsuura |
| 4,840,187 | A | 6/1989 | Brazier |
| 4,842,594 | A | 6/1989 | Ness |
| 4,848,364 | A | 7/1989 | Bosman |
| 4,863,449 | A | 9/1989 | Therriault et al. |
| 4,871,611 | A | 10/1989 | LeBel |
| 4,872,450 | A | 10/1989 | Austad |
| 4,878,901 | A | 11/1989 | Sachse |
| 4,897,081 | A | 1/1990 | Poirier et al. |
| 4,906,233 | A | 3/1990 | Moriuchi et al. |
| 4,906,240 | A | 3/1990 | Reed et al. |
| 4,919,654 | A | 4/1990 | Kalt |
| 4,930,997 | A | 6/1990 | Bennett |
| 4,941,882 | A | 7/1990 | Ward et al. |
| 4,953,565 | A | 9/1990 | Tachibana et al. |
| 4,961,493 | A | 10/1990 | Kaihatsu |
| 4,969,880 | A | 11/1990 | Zamierowski |
| 4,981,474 | A | 1/1991 | Bopp et al. |
| 4,985,019 | A | 1/1991 | Michelson |
| 4,995,382 | A | 2/1991 | Lang et al. |
| 4,996,128 | A | 2/1991 | Aldecoa et al. |
| 5,010,883 | A | 4/1991 | Rawlings et al. |
| 5,018,515 | A | 5/1991 | Gilman |
| 5,025,783 | A | 6/1991 | Lamb |
| 5,028,597 | A | 7/1991 | Kodama et al. |
| 5,037,397 | A | 8/1991 | Kalt et al. |
| 5,042,500 | A | 8/1991 | Norlien et al. |
| 5,086,170 | A | 2/1992 | Luheshi et al. |
| 5,092,323 | A | 3/1992 | Riedel et al. |
| 5,092,858 | A | 3/1992 | Benson et al. |
| 5,100,396 | A | 3/1992 | Zamierowski |
| 5,112,323 | A | 5/1992 | Winkler et al. |
| 5,127,601 | A | 7/1992 | Schroeder |
| 5,134,994 | A | 8/1992 | Say |
| 5,149,331 | A | 9/1992 | Ferdman et al. |
| 5,151,314 | A | 9/1992 | Brown |
| 5,152,757 | A | 10/1992 | Eriksson |
| 5,167,613 | A * | 12/1992 | Karami ............... A61F 13/0203 602/42 |
| 5,176,663 | A | 1/1993 | Svedman et al. |
| 5,180,375 | A | 1/1993 | Feibus |
| 5,215,522 | A | 6/1993 | Page et al. |
| 5,232,453 | A | 8/1993 | Plass et al. |
| 5,244,457 | A | 9/1993 | Karami et al. |
| 5,246,775 | A | 9/1993 | Loscuito |
| 5,261,893 | A | 11/1993 | Zamierowski |
| 5,266,372 | A | 11/1993 | Arakawa et al. |
| 5,270,358 | A | 12/1993 | Asmus |
| 5,271,987 | A * | 12/1993 | Iskra .................... A61F 13/515 428/192 |
| 5,278,100 | A | 1/1994 | Doan et al. |
| 5,279,550 | A | 1/1994 | Habib et al. |
| 5,298,015 | A | 3/1994 | Komatsuzaki et al. |
| 5,342,329 | A | 8/1994 | Croquevielle |
| 5,342,376 | A | 8/1994 | Ruff |
| 5,344,415 | A | 9/1994 | DeBusk et al. |
| 5,356,386 | A | 10/1994 | Goldberg et al. |
| 5,358,494 | A | 10/1994 | Svedman |
| 5,384,174 | A | 1/1995 | Ward et al. |
| 5,387,207 | A | 2/1995 | Dyer et al. |
| 5,419,769 | A | 5/1995 | Devlin et al. |
| 5,423,778 | A | 6/1995 | Eriksson et al. |
| 5,429,590 | A | 7/1995 | Saito et al. |
| 5,437,622 | A | 8/1995 | Carion |
| 5,437,651 | A | 8/1995 | Todd et al. |
| 5,445,604 | A | 8/1995 | Lang |
| 5,447,492 | A * | 9/1995 | Cartmell ............. A61F 13/0203 602/41 |
| 5,458,938 | A | 10/1995 | Nygard et al. |
| 5,501,212 | A | 3/1996 | Psaros |

(56) References Cited

U.S. PATENT DOCUMENTS

| | | |
|---|---|---|
| 5,522,808 A | 6/1996 | Skalla |
| 5,527,293 A | 6/1996 | Zamierowski |
| 5,549,584 A | 8/1996 | Gross |
| 5,549,585 A | 8/1996 | Maher et al. |
| 5,556,375 A | 9/1996 | Ewall |
| 5,585,178 A | 12/1996 | Calhoun et al. |
| 5,599,292 A | 2/1997 | Yoon |
| 5,607,388 A | 3/1997 | Ewall |
| 5,611,373 A | 3/1997 | Ashcraft |
| 5,634,893 A | 6/1997 | Rishton |
| 5,636,643 A | 6/1997 | Argenta et al. |
| 5,641,506 A | 6/1997 | Talke et al. |
| 5,645,081 A | 7/1997 | Argenta et al. |
| 5,653,224 A | 8/1997 | Johnson |
| 5,678,564 A | 10/1997 | Lawrence et al. |
| 5,710,233 A | 1/1998 | Meckel et al. |
| 5,714,225 A | 2/1998 | Hansen et al. |
| 5,736,470 A | 4/1998 | Schneberger et al. |
| 5,759,570 A | 6/1998 | Arnold |
| 5,776,119 A | 7/1998 | Bilbo et al. |
| 5,807,295 A | 9/1998 | Hutcheon et al. |
| 5,830,201 A | 11/1998 | George et al. |
| 5,878,971 A | 3/1999 | Minnema |
| 5,902,439 A | 5/1999 | Pike et al. |
| 5,919,476 A | 7/1999 | Fischer et al. |
| 5,941,863 A | 8/1999 | Guidotti et al. |
| 5,964,252 A | 10/1999 | Simmons et al. |
| 5,981,822 A | 11/1999 | Addison |
| 5,998,561 A | 12/1999 | Jada |
| 6,071,267 A | 6/2000 | Zamierowski |
| 6,083,616 A | 7/2000 | Dressler |
| 6,086,995 A | 7/2000 | Smith |
| 6,135,116 A | 10/2000 | Vogel et al. |
| 6,174,306 B1 | 1/2001 | Fleischmann |
| 6,191,335 B1 | 2/2001 | Robinson |
| 6,201,164 B1 | 3/2001 | Wulff et al. |
| 6,228,485 B1 | 5/2001 | Leiter |
| 6,238,762 B1 | 5/2001 | Friedland et al. |
| 6,241,747 B1 | 6/2001 | Ruff |
| 6,262,329 B1 | 7/2001 | Brunsveld et al. |
| 6,287,316 B1 | 9/2001 | Agarwal et al. |
| 6,345,623 B1 | 2/2002 | Heaton et al. |
| 6,457,200 B1 * | 10/2002 | Tanaka ............... B08B 7/0028 15/104.002 |
| 6,458,109 B1 * | 10/2002 | Henley ............... A61M 35/30 604/304 |
| 6,488,643 B1 | 12/2002 | Tumey et al. |
| 6,493,568 B1 | 12/2002 | Bell et al. |
| 6,495,229 B1 | 12/2002 | Carte et al. |
| 6,503,855 B1 | 1/2003 | Menzies et al. |
| 6,548,727 B1 | 4/2003 | Swenson |
| 6,553,998 B2 | 4/2003 | Heaton et al. |
| 6,566,575 B1 | 5/2003 | Stickels et al. |
| 6,566,577 B1 | 5/2003 | Addison et al. |
| 6,626,891 B2 | 9/2003 | Ohmstede |
| 6,627,215 B1 | 9/2003 | Dale et al. |
| 6,648,862 B2 | 11/2003 | Watson |
| 6,680,113 B1 | 1/2004 | Lucast et al. |
| 6,685,681 B2 | 2/2004 | Lockwood et al. |
| 6,693,180 B2 | 2/2004 | Lee et al. |
| 6,695,823 B1 | 2/2004 | Lina et al. |
| 6,752,794 B2 | 6/2004 | Lockwood et al. |
| 6,787,682 B2 * | 9/2004 | Gilman ............... A61F 13/023 602/42 |
| 6,814,079 B2 | 11/2004 | Heaton et al. |
| 6,855,135 B2 | 2/2005 | Lockwood et al. |
| 6,856,821 B2 | 2/2005 | Johnson |
| 6,979,324 B2 | 12/2005 | Bybordi et al. |
| 7,070,584 B2 * | 7/2006 | Johnson ............... A61M 1/784 604/313 |
| 7,154,017 B2 | 12/2006 | Sigurjonsson et al. |
| 7,402,721 B2 | 7/2008 | Sigurjonsson et al. |
| 7,569,742 B2 | 8/2009 | Haggstrom et al. |
| 7,645,269 B2 | 1/2010 | Zamierowski |
| 7,846,141 B2 | 12/2010 | Weston |
| 8,062,273 B2 | 11/2011 | Weston |
| 8,216,198 B2 | 7/2012 | Heagle et al. |
| 8,251,979 B2 | 8/2012 | Malhi |
| 8,257,327 B2 | 9/2012 | Blott et al. |
| 8,298,197 B2 | 10/2012 | Eriksson et al. |
| 8,398,614 B2 | 3/2013 | Blott et al. |
| 8,449,509 B2 | 5/2013 | Weston |
| 8,529,532 B2 | 9/2013 | Pinto et al. |
| 8,529,548 B2 | 9/2013 | Blott et al. |
| 8,535,296 B2 | 9/2013 | Blott et al. |
| 8,551,060 B2 | 10/2013 | Schuessler et al. |
| 8,568,386 B2 | 10/2013 | Malhi |
| 8,632,523 B2 | 1/2014 | Eriksson et al. |
| 8,679,081 B2 | 3/2014 | Heagle et al. |
| 8,764,732 B2 * | 7/2014 | Hartwell ............... A61F 13/0206 604/543 |
| 8,834,451 B2 | 9/2014 | Blott et al. |
| 8,920,830 B2 | 12/2014 | Mathies |
| 8,926,592 B2 | 1/2015 | Blott et al. |
| 9,017,302 B2 | 4/2015 | Vitaris et al. |
| 9,192,444 B2 | 11/2015 | Locke et al. |
| 9,198,801 B2 | 12/2015 | Weston |
| 9,211,365 B2 | 12/2015 | Weston |
| 9,289,542 B2 | 3/2016 | Blott et al. |
| 9,877,873 B2 | 1/2018 | Coulthard et al. |
| 9,956,120 B2 * | 5/2018 | Locke ............... A61F 13/00063 604/313 |
| 2001/0030304 A1 | 10/2001 | Kohda et al. |
| 2001/0051178 A1 | 12/2001 | Blatchford et al. |
| 2002/0009568 A1 | 1/2002 | Bries et al. |
| 2002/0016346 A1 | 2/2002 | Brandt et al. |
| 2002/0065494 A1 * | 5/2002 | Lockwood ............... A61M 1/90 604/313 |
| 2002/0077661 A1 | 6/2002 | Saadat |
| 2002/0090496 A1 | 7/2002 | Kim et al. |
| 2002/0115951 A1 | 8/2002 | Norstrem et al. |
| 2002/0119292 A1 | 8/2002 | Venkatasanthanam et al. |
| 2002/0120185 A1 | 8/2002 | Johnson |
| 2002/0130064 A1 | 9/2002 | Adams et al. |
| 2002/0143286 A1 | 10/2002 | Tumey |
| 2002/0150270 A1 | 10/2002 | Werner |
| 2002/0150720 A1 | 10/2002 | Howard et al. |
| 2002/0161346 A1 | 10/2002 | Lockwood et al. |
| 2002/0164346 A1 | 11/2002 | Nicolette |
| 2002/0183702 A1 | 12/2002 | Henley et al. |
| 2002/0198504 A1 | 12/2002 | Risk et al. |
| 2003/0014022 A1 | 1/2003 | Lockwood et al. |
| 2003/0070680 A1 | 4/2003 | Smith et al. |
| 2003/0109855 A1 | 6/2003 | Solem et al. |
| 2003/0158577 A1 | 8/2003 | Ginn et al. |
| 2003/0208175 A1 | 11/2003 | Gross et al. |
| 2003/0212357 A1 | 11/2003 | Pace |
| 2003/0225347 A1 | 12/2003 | Argenta et al. |
| 2003/0225355 A1 | 12/2003 | Butler |
| 2004/0002676 A1 | 1/2004 | Siegwart et al. |
| 2004/0030304 A1 * | 2/2004 | Hunt ............... A61F 13/0216 604/317 |
| 2004/0064132 A1 | 4/2004 | Boehringer et al. |
| 2004/0077984 A1 | 4/2004 | Worthley |
| 2004/0082925 A1 | 4/2004 | Patel |
| 2004/0099268 A1 | 5/2004 | Smith et al. |
| 2004/0118401 A1 | 6/2004 | Smith et al. |
| 2004/0127836 A1 | 7/2004 | Sigurjonsson et al. |
| 2004/0127862 A1 | 7/2004 | Bubb et al. |
| 2004/0133143 A1 | 7/2004 | Burton et al. |
| 2004/0163278 A1 | 8/2004 | Caspers et al. |
| 2004/0186239 A1 | 9/2004 | Qin et al. |
| 2004/0219337 A1 | 11/2004 | Langley et al. |
| 2004/0230179 A1 | 11/2004 | Shehada |
| 2005/0034731 A1 | 2/2005 | Rousseau et al. |
| 2005/0054998 A1 | 3/2005 | Poccia et al. |
| 2005/0059918 A1 | 3/2005 | Sigurjonsson et al. |
| 2005/0065484 A1 | 3/2005 | Watson |
| 2005/0070858 A1 | 3/2005 | Lockwood et al. |
| 2005/0101940 A1 | 5/2005 | Radl et al. |
| 2005/0113732 A1 | 5/2005 | Lawry |
| 2005/0124925 A1 | 6/2005 | Scherpenborg |
| 2005/0131327 A1 | 6/2005 | Lockwood et al. |
| 2005/0137539 A1 | 6/2005 | Biggie et al. |

(56) References Cited

U.S. PATENT DOCUMENTS

| | | |
|---|---|---|
| 2005/0143694 A1 | 6/2005 | Schmidt et al. |
| 2005/0158442 A1 | 7/2005 | Westermann et al. |
| 2005/0159695 A1 | 7/2005 | Cullen et al. |
| 2005/0161042 A1 | 7/2005 | Fudge et al. |
| 2005/0163978 A1 | 7/2005 | Strobech et al. |
| 2005/0214376 A1 | 9/2005 | Faure et al. |
| 2005/0233072 A1 | 10/2005 | Stephan et al. |
| 2005/0256437 A1 | 11/2005 | Silcock et al. |
| 2005/0261642 A1 | 11/2005 | Weston |
| 2005/0261643 A1 | 11/2005 | Bybordi et al. |
| 2005/0277860 A1 | 12/2005 | Jensen |
| 2006/0014030 A1 | 1/2006 | Langen et al. |
| 2006/0020235 A1 | 1/2006 | Siniaguine |
| 2006/0079852 A1 | 4/2006 | Bubb et al. |
| 2006/0083776 A1 | 4/2006 | Bolt et al. |
| 2006/0154546 A1 | 7/2006 | Murphy et al. |
| 2006/0236979 A1 | 10/2006 | Stolarz et al. |
| 2006/0241542 A1 | 10/2006 | Gudnason et al. |
| 2006/0271020 A1 | 11/2006 | Huang et al. |
| 2007/0027414 A1 | 2/2007 | Hoffman et al. |
| 2007/0028526 A1 | 2/2007 | Woo et al. |
| 2007/0078366 A1 | 4/2007 | Haggstrom et al. |
| 2007/0161937 A1 | 7/2007 | Aali |
| 2007/0185426 A1 | 8/2007 | Ambrosio et al. |
| 2007/0190281 A1 | 8/2007 | Hooft |
| 2007/0225663 A1 | 9/2007 | Watt et al. |
| 2007/0265585 A1 | 11/2007 | Joshi et al. |
| 2007/0265586 A1 | 11/2007 | Joshi et al. |
| 2007/0283962 A1 | 12/2007 | Doshi et al. |
| 2008/0009812 A1 | 1/2008 | Riesinger |
| 2008/0027366 A1 | 1/2008 | Da Silva Macedo |
| 2008/0082059 A1 | 4/2008 | Fink et al. |
| 2008/0090085 A1 | 4/2008 | Kawate et al. |
| 2008/0119802 A1 | 5/2008 | Riesinger |
| 2008/0138591 A1 | 6/2008 | Graham et al. |
| 2008/0149104 A1 | 6/2008 | Eifler |
| 2008/0173389 A1 | 7/2008 | Mehta et al. |
| 2008/0195017 A1 | 8/2008 | Robinson et al. |
| 2008/0225663 A1 | 9/2008 | Smith et al. |
| 2008/0243044 A1 | 10/2008 | Hunt et al. |
| 2008/0269657 A1 | 10/2008 | Brenneman et al. |
| 2008/0271804 A1 | 11/2008 | Biggie et al. |
| 2009/0025724 A1 | 1/2009 | Herron, Jr. |
| 2009/0088719 A1 | 4/2009 | Driskell |
| 2009/0093779 A1 | 4/2009 | Riesinger |
| 2009/0124988 A1 | 5/2009 | Coulthard |
| 2009/0177172 A1 | 7/2009 | Wilkes |
| 2009/0216168 A1 | 8/2009 | Eckstein |
| 2009/0216170 A1 | 8/2009 | Robinson et al. |
| 2009/0216204 A1 | 8/2009 | Bhavaraju et al. |
| 2009/0227969 A1* | 9/2009 | Jaeb .................. A61M 1/962 604/313 |
| 2009/0234306 A1* | 9/2009 | Vitaris ............... A61F 13/0243 604/304 |
| 2009/0234307 A1 | 9/2009 | Vitaris |
| 2009/0264807 A1 | 10/2009 | Haggstrom et al. |
| 2009/0292264 A1 | 11/2009 | Hudspeth et al. |
| 2009/0312662 A1 | 12/2009 | Colman et al. |
| 2009/0326487 A1 | 12/2009 | Vitaris |
| 2009/0326488 A1 | 12/2009 | Budig et al. |
| 2010/0028390 A1* | 2/2010 | Cleary ............... A61M 37/0015 424/400 |
| 2010/0030170 A1 | 2/2010 | Keller et al. |
| 2010/0063467 A1 | 3/2010 | Addison et al. |
| 2010/0069863 A1* | 3/2010 | Olson ................ A61F 13/00987 604/368 |
| 2010/0106106 A1* | 4/2010 | Heaton ............... A61B 17/0057 604/290 |
| 2010/0106118 A1 | 4/2010 | Heaton et al. |
| 2010/0125259 A1 | 5/2010 | Olson |
| 2010/0159192 A1 | 6/2010 | Cotton |
| 2010/0168633 A1 | 7/2010 | Bougherara et al. |
| 2010/0168635 A1 | 7/2010 | Freiding et al. |
| 2010/0185163 A1 | 7/2010 | Heagle |
| 2010/0212768 A1 | 8/2010 | Resendes |
| 2010/0226824 A1 | 9/2010 | Ophir et al. |
| 2010/0262090 A1 | 10/2010 | Riesinger |
| 2010/0267302 A1 | 10/2010 | Kantner et al. |
| 2010/0268144 A1 | 10/2010 | Lu et al. |
| 2010/0286582 A1 | 11/2010 | Simpson et al. |
| 2010/0305490 A1* | 12/2010 | Coulthard ............ A61F 13/022 602/43 |
| 2010/0305524 A1 | 12/2010 | Vess et al. |
| 2010/0312159 A1 | 12/2010 | Aali et al. |
| 2010/0318072 A1 | 12/2010 | Johnston et al. |
| 2010/0324516 A1 | 12/2010 | Braga et al. |
| 2011/0046585 A1 | 2/2011 | Weston |
| 2011/0054423 A1 | 3/2011 | Blott et al. |
| 2011/0118683 A1 | 5/2011 | Weston |
| 2011/0137271 A1* | 6/2011 | Andresen ............. A61F 13/023 604/319 |
| 2011/0160686 A1 | 6/2011 | Ueda et al. |
| 2011/0171480 A1 | 7/2011 | Mori et al. |
| 2011/0172617 A1 | 7/2011 | Riesinger |
| 2011/0201984 A1 | 8/2011 | Dubrow et al. |
| 2011/0224631 A1* | 9/2011 | Simmons .......... A61F 13/00021 604/319 |
| 2011/0229688 A1 | 9/2011 | Cotton |
| 2011/0237969 A1 | 9/2011 | Eckerbom et al. |
| 2011/0244010 A1 | 10/2011 | Doshi |
| 2011/0257612 A1 | 10/2011 | Locke et al. |
| 2011/0257617 A1 | 10/2011 | Franklin |
| 2011/0281084 A1 | 11/2011 | Ashwell |
| 2011/0282309 A1* | 11/2011 | Adie ................ A61F 13/00068 604/319 |
| 2012/0016322 A1 | 1/2012 | Coulthard et al. |
| 2012/0019031 A1 | 1/2012 | Bessert |
| 2012/0036733 A1 | 2/2012 | Dehn |
| 2012/0040131 A1 | 2/2012 | Speer |
| 2012/0059339 A1 | 3/2012 | Gundersen |
| 2012/0095380 A1 | 4/2012 | Gergely et al. |
| 2012/0109034 A1 | 5/2012 | Locke et al. |
| 2012/0123359 A1 | 5/2012 | Reed |
| 2012/0143157 A1 | 6/2012 | Riesinger |
| 2012/0237722 A1 | 9/2012 | Seyler et al. |
| 2012/0258271 A1 | 10/2012 | Maughan |
| 2012/0310186 A1 | 12/2012 | Moghe et al. |
| 2013/0030394 A1 | 1/2013 | Locke et al. |
| 2013/0053746 A1 | 2/2013 | Roland et al. |
| 2013/0066285 A1 | 3/2013 | Locke et al. |
| 2013/0096518 A1 | 4/2013 | Hall et al. |
| 2013/0098360 A1 | 4/2013 | Hurmez et al. |
| 2013/0116661 A1 | 5/2013 | Coward et al. |
| 2013/0150763 A1 | 6/2013 | Mirzaei et al. |
| 2013/0152945 A1 | 6/2013 | Locke et al. |
| 2013/0165887 A1 | 6/2013 | Schickli et al. |
| 2013/0172843 A1 | 7/2013 | Kurata |
| 2013/0189339 A1 | 7/2013 | Vachon |
| 2013/0261585 A1 | 10/2013 | Lee |
| 2013/0304007 A1 | 11/2013 | Toth |
| 2013/0330486 A1 | 12/2013 | Shields |
| 2014/0039423 A1 | 2/2014 | Riesinger |
| 2014/0039424 A1 | 2/2014 | Locke |
| 2014/0058309 A1 | 2/2014 | Addison et al. |
| 2014/0107561 A1 | 4/2014 | Dorian et al. |
| 2014/0107562 A1 | 4/2014 | Dorian et al. |
| 2014/0141197 A1 | 5/2014 | Hill et al. |
| 2014/0155849 A1 | 6/2014 | Heaton et al. |
| 2014/0163491 A1 | 6/2014 | Schuessler et al. |
| 2014/0171851 A1 | 6/2014 | Addison |
| 2014/0178564 A1 | 6/2014 | Patel |
| 2014/0309574 A1 | 10/2014 | Cotton |
| 2014/0336557 A1 | 11/2014 | Durdag et al. |
| 2014/0350494 A1* | 11/2014 | Hartwell ............ A61F 13/00068 604/319 |
| 2014/0352073 A1 | 12/2014 | Goenka |
| 2015/0030848 A1 | 1/2015 | Goubard |
| 2015/0045752 A1 | 2/2015 | Grillitsch et al. |
| 2015/0057625 A1* | 2/2015 | Coulthard .......... A61F 13/0216 604/319 |
| 2015/0080788 A1 | 3/2015 | Blott et al. |
| 2015/0080815 A1 | 3/2015 | Chakravarthy et al. |

(56) References Cited

U.S. PATENT DOCUMENTS

| | | | |
|---|---|---|---|
| 2015/0119830 A1* | 4/2015 | Luckemeyer | A61M 1/90 604/319 |
| 2015/0119833 A1* | 4/2015 | Coulthard | A61F 13/00068 604/319 |
| 2015/0119834 A1 | 4/2015 | Locke et al. | |
| 2015/0141941 A1 | 5/2015 | Allen et al. | |
| 2015/0190286 A1 | 7/2015 | Allen et al. | |
| 2015/0290041 A1 | 10/2015 | Richard | |
| 2016/0000610 A1 | 1/2016 | Riesinger | |
| 2016/0067107 A1 | 3/2016 | Cotton | |
| 2016/0144084 A1 | 5/2016 | Collinson et al. | |

FOREIGN PATENT DOCUMENTS

| | | |
|---|---|---|
| AU | 755496 B2 | 12/2002 |
| AU | 2009200608 A1 | 10/2009 |
| CA | 2005436 A1 | 6/1990 |
| CN | 87101823 A | 8/1988 |
| DE | 26 40 413 A1 | 3/1978 |
| DE | 43 06 478 A1 | 9/1994 |
| DE | 29 504 378 U1 | 9/1995 |
| DE | 202004018245 U1 | 7/2005 |
| DE | 202014100383 U1 | 2/2015 |
| EP | 0097517 A1 | 1/1984 |
| EP | 0100148 A1 | 2/1984 |
| EP | 0117632 A2 | 9/1984 |
| EP | 0161865 A2 | 11/1985 |
| EP | 0251810 A2 | 1/1988 |
| EP | 0275353 A2 | 7/1988 |
| EP | 0358302 A2 | 3/1990 |
| EP | 0538917 A1 | 4/1993 |
| EP | 0630629 A1 | 12/1994 |
| EP | 0659390 A2 | 6/1995 |
| EP | 0633758 B1 | 10/1996 |
| EP | 1002846 A1 | 5/2000 |
| EP | 1018967 A1 | 7/2000 |
| EP | 2578193 A1 | 4/2013 |
| GB | 692578 A | 6/1953 |
| GB | 1386800 A | 3/1975 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| GB | 2377939 A | 1/2003 |
| GB | 2392836 A | 3/2004 |
| GB | 2393655 A | 4/2004 |
| GB | 2425487 A | 11/2006 |
| GB | 2452720 A | 3/2009 |
| GB | 2496310 A | 5/2013 |
| JP | 1961003393 | 2/1961 |
| JP | S62139523 U | 9/1987 |
| JP | S62-275456 A | 11/1987 |
| JP | 2005205120 A | 8/2005 |
| JP | 2007254515 A | 10/2007 |
| JP | 4129536 B2 | 8/2008 |
| JP | 2012050274 A | 3/2012 |
| SG | 71559 | 4/2002 |
| WO | 80/02182 A1 | 10/1980 |
| WO | 87/04626 A1 | 8/1987 |
| WO | 8707164 A1 | 12/1987 |
| WO | 90/010424 A1 | 9/1990 |
| WO | 93/009727 A1 | 5/1993 |
| WO | 94/020041 A1 | 9/1994 |
| WO | 96/05873 A1 | 2/1996 |
| WO | 9622753 A1 | 8/1996 |
| WO | 97/18007 A1 | 5/1997 |
| WO | 99/13793 A1 | 3/1999 |
| WO | 99/65542 A1 | 12/1999 |
| WO | 01/36188 A1 | 5/2001 |
| WO | 01/60296 A1 | 8/2001 |
| WO | 0168021 A1 | 9/2001 |
| WO | 0185248 A1 | 11/2001 |
| WO | 0190465 A2 | 11/2001 |
| WO | 0243743 A1 | 6/2002 |
| WO | 02062403 A1 | 8/2002 |
| WO | 03-018098 A2 | 3/2003 |
| WO | 03045294 A1 | 6/2003 |
| WO | 03045492 A1 | 6/2003 |
| WO | 03053484 A1 | 7/2003 |
| WO | 2004024197 A1 | 3/2004 |
| WO | 2004037334 A1 | 5/2004 |
| WO | 2004112852 A1 | 12/2004 |
| WO | 2005002483 A2 | 1/2005 |
| WO | 2005062896 A2 | 7/2005 |
| WO | 2005105176 A1 | 11/2005 |
| WO | 2005123170 A1 | 12/2005 |
| WO | 2007022097 A2 | 2/2007 |
| WO | 2007030601 A2 | 3/2007 |
| WO | 2007070269 A1 | 6/2007 |
| WO | 2007085396 A1 | 8/2007 |
| WO | 2007087811 A1 | 8/2007 |
| WO | 2007113597 A2 | 10/2007 |
| WO | 2007133618 A2 | 11/2007 |
| WO | 2008026117 A1 | 3/2008 |
| WO | 2008/041926 A1 | 4/2008 |
| WO | 2008048527 A2 | 4/2008 |
| WO | 2008054312 A1 | 5/2008 |
| WO | 2008/082444 A2 | 7/2008 |
| WO | 2008/100440 A1 | 8/2008 |
| WO | 2008104609 A1 | 9/2008 |
| WO | 2008/131895 A1 | 11/2008 |
| WO | 2009/002260 A1 | 12/2008 |
| WO | 2008149107 A1 | 12/2008 |
| WO | 2009066105 A1 | 5/2009 |
| WO | 2009066106 A1 | 5/2009 |
| WO | 2009081134 A1 | 7/2009 |
| WO | 2009089016 A1 | 7/2009 |
| WO | 2009/124100 A1 | 10/2009 |
| WO | 2009126103 A1 | 10/2009 |
| WO | 2010011148 A1 | 1/2010 |
| WO | 2010016791 A1 | 2/2010 |
| WO | 2010032728 A1 | 3/2010 |
| WO | 2010/056977 A2 | 5/2010 |
| WO | 2010129299 A2 | 11/2010 |
| WO | 2011008497 A2 | 1/2011 |
| WO | 2011/049562 A1 | 4/2011 |
| WO | 2011043786 A1 | 4/2011 |
| WO | 2011115908 A1 | 9/2011 |
| WO | 2011121127 A1 | 10/2011 |
| WO | 2011130570 A1 | 10/2011 |
| WO | 2011162862 A1 | 12/2011 |
| WO | 2012/112204 A1 | 8/2012 |
| WO | 2012104584 A1 | 8/2012 |
| WO | 2012140378 A1 | 10/2012 |
| WO | 2012143665 A1 | 10/2012 |
| WO | 2013009239 A1 | 1/2013 |
| WO | 2013066426 A2 | 5/2013 |
| WO | 2013090810 A1 | 6/2013 |
| WO | 2014022400 A1 | 2/2014 |
| WO | 2014039557 A1 | 3/2014 |
| WO | 2014078518 A1 | 5/2014 |
| WO | 2014/113253 A1 | 7/2014 |
| WO | 2014140608 A1 | 9/2014 |
| WO | 2014143488 A1 | 9/2014 |
| WO | 2015/065615 A1 | 5/2015 |
| WO | 2015130471 A1 | 9/2015 |
| WO | 2017048866 A1 | 3/2017 |

OTHER PUBLICATIONS

Office Action for related U.S. Appl. No. 14/630,290, dated Apr. 30, 2020.

Office Action for related U.S. Appl. No. 15/793,044, dated May 13, 2020.

EP Informal Search Report for related application 19186600.3, received May 11, 2020.

Office Action for related U.S. Appl. No. 15/884,198, dated May 19, 2020.

International Search Report and Written Opinion dated Oct. 19, 2010; PCT International Application No. PCT/US2009/036217.

(56) References Cited

OTHER PUBLICATIONS

NPD 1000 Negative Pressure Would Therapy System, Kalypto Medical, pp. 1-4, dated Sep. 2008.
International Search Report and Written Opinion for PCT/GB2008/003075 dated Mar. 11, 2010.
International Search Report and Written Opinion for PCT/GB2008/004216 dated Jul. 2, 2009.
International Search Report and Written Opinion for PCT/GB2012/000099 dated May 2, 2012.
EP Examination Report for corresponding application 12705381.7, dated May 22, 2014.
International Search Report and Written Opinion for PCT/US2012/069893 dated Apr. 8, 2013.
International Search Report and Written Opinion for PCT/US2013/070070 dated Jan. 29, 2014.
International Search Report and Written Opinion for PCT/US2014/016320 dated Apr. 15, 2014.
International Search Report and Written Opinion for PCT/US2014/056566 dated Dec. 5, 2014.
International Search Report and Written Opinion for PCT/US2014/056508 dated Dec. 9, 2014.
International Search Report and Written Opinion for PCT/US2014/056524 dated Dec. 11, 2014.
International Search Report and Written Opinion for PCT/US2014/056594 dated Dec. 2, 2014.
International Search Report and Written opinion for PCT Application PCT/US2009/036222, dated Dec. 15, 2009.
International Search Report and Written Opinion for PCT/US2014/061251 dated May 8, 2015.
International Search Report and Written Opinion for PCT/IB2013/060862 dated Jun. 26, 2014.
International Search Report and Written Opinion for PCT/US2015/015493 dated May 4, 2015.
Extended European Search Report for corresponding Application No. 15194949.2, dated Mar. 11, 2016.
European Search Report for corresponding EPSN 15157408.4 published on Sep. 30, 2015.
International Search Report and Written Opinion for PCT/US2015/034289 dated Aug. 21, 2015.
International Search Report and Written Opinion for PCT/US2015/065135 dated Apr. 4, 2016.
International Search Report and Written Opinion for PCT/GB2012/050822 dated Aug. 8, 2012.
International Search Report and Written Opinion for PCT/US2015/029037 dated Sep. 4, 2015.
International Search Report and Written Opinion for PCT International Application No. PCT/US2011/028344, dated Jun. 1, 2011.
European Search Report for EP 11714148.1, dated May 2, 2014.
European Search Report for corresponding Application No. 15192606.0 dated Feb. 24, 2016.
International Search Report and Written Opinion for corresponding PCT/US2014/048081 dated Nov. 14, 2014.
International Search Report and Written Opinion for corresponding PCT/US2014/010704 dated Mar. 25, 2014.
European Examination Report dated Jun. 29, 2016, corresponding to EP Application No. 16173614.5.
International Search Report and Written Opinion for corresponding PCT application PCT/US2016/051768 dated Dec. 15, 2016.
European Search Report for corresponding EP Application 171572787 dated Jun. 6, 2017.
International Search Report and Written Opinion for corresponding application PCT/US2016/031397, dated Aug. 8, 2016.
European Search Report for corresponding application 17167872.5, dated Aug. 14, 2017.
M. Waring et al., "Cell attachment to adhesive dressing: qualitative and quantitative analysis", Wounds, UK, (2008), vol. 4, No. 3, pp. 35-47.
R. White, "Evidence for atraumatic soft silicone wound dressing use". Wound, UK (2005), vol. 3, pp. 104-108, Mepilex Border docs, (2001).
European Search Report for corresponding application 17183683.6, dated Sep. 18, 2017.
European Search Report for corresponding application 17164033.7, dated Oct. 13, 2017.
Extended European Search Report for corresponding application 17191970.7, dated Oct. 26, 2017.
Japanese office action for related application 2015-547246, dated Sep. 5, 2017.
Office Action for related U.S. Appl. No. 13/982,650, dated Dec. 14, 2017.
Australian Office Action for related application 2013344686, dated Nov. 28, 2017.
Office Action for related U.S. Appl. No. 14/517,521, dated Dec. 12, 2017.
Office Action for related U.S. Appl. No. 14/490,898, dated Jan. 4, 2018.
International Search Report and Written Opinion for related application PCT/US2017/058209, dated Jan. 10, 2018.
Office Action for related U.S. Appl. No. 14/965,675, dated Jan. 31, 2018.
International Search Report and Written Opinion for related application PCT/US2016/047351, dated Nov. 2, 2016.
Extended European Search Report for related application 17177013.4, dated Mar. 19, 2018.
Extended European Search Report for related application 16793298.7, dated Mar. 27, 2018.
Office Action for related U.S. Appl. No. 14/965,675, dated Aug. 9, 2018.
Office Action for related U.S. Appl. No. 15/307,472, dated Oct. 18, 2018.
Office Action for related U.S. Appl. No. 16/007,060, dated Aug. 18, 2020.
Office Action for related U.S. Appl. No. 15/937,485, dated Aug. 4, 2020.
Office Action for related U.S. Appl. No. 15/793,044, dated Sep. 24, 2020.
Extended European Search Report for related application 20185730.7, dated Oct. 9, 2020.
Office Action for related U.S. Appl. No. 15/314,426, dated Aug. 29, 2019.
Office Action for related U.S. Appl. No. 14/965,675, dated Dec. 12, 2018.
Office Action for related U.S. Appl. No. 14/619,714, dated Dec. 3, 2018.
Office Action for related U.S. Appl. No. 14/630,290, dated Jan. 11, 2019.
Office Action for related U.S. Appl. No. 15/265,718, dated Feb. 7, 2019.
Extended European Search Report for related application 18193559.4, dated Dec. 17, 2018.
Office Action for related U.S. Appl. No. 14/080,348, dated Apr. 12, 2019.
Japanese Notice of Rejection for related application 2016-570333, dated Feb. 26, 2019.
Office Action for related U.S. Appl. No. 15/410,991, dated May 2, 2019.
Office Action for related U.S. Appl. No. 15/600,451, dated Nov. 27, 2019.
Louis C. Argenta, MD and Michael J. Morykwas, PHD; Vacuum-Assisted Closure: A New Method for Wound Control and Treatment: Clinical Experience; Annals of Plastic Surgery; vol. 38, No. 6, Jun. 1997; pp. 563-576.
Susan Mendez-Eatmen, RN; "When wounds Won't Heal" RN Jan. 1998, vol. 61 (1); Medical Economics Company, Inc., Montvale, NJ, USA; pp. 20-24.
James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.
John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

(56) References Cited

OTHER PUBLICATIONS

S.E. Greer, et al. "The Use of Subatmospheric Pressure Dressing Therapy to Close Lymphocutaneous Fistulas of the Groin" British Journal of Plastic Surgery (2000), 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; dated Nov. 23, 1995.
PCT International Search Report for PCT International Application PCT/GB98/02713; dated Jan. 8, 1999.
PCT Written Opinion; PCT International Application PCT/GB98/02713; dated Jun. 8, 1999.
PCT International Examination and Search Report, PCT International Application PCT/GB96/02802; dated Jan. 15, 1998 & Apr. 29, 1997.
PCT Written Opinion, PCT International Application PCT/GB96/02802; dated Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu.N., et al; "Active Wound Drainage", Vestnki Khirurgi, vol. 138, Issue 4, 1987, and 7 page English translation thereof.
Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.
Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.
N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96.
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinoví?, V. ?uki?, Ž. Maksimoví?, ?. Radak, and P. Peška, "Vacuum Therapy in the Treatment of Peripheral Blood Vessels," Timok Medical Journal 11 (1986), pp. 161-164.
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C. ® Therapy Clinical Guidelines: A Reference Source for Clinicians; Jul. 2007.
Advisory Action for related U.S. Appl. No. 15/793,044, dated Dec. 9, 2020.
Office Action for related U.S. Appl. No. 16/151,005, dated Apr. 13, 2021.

\* cited by examiner

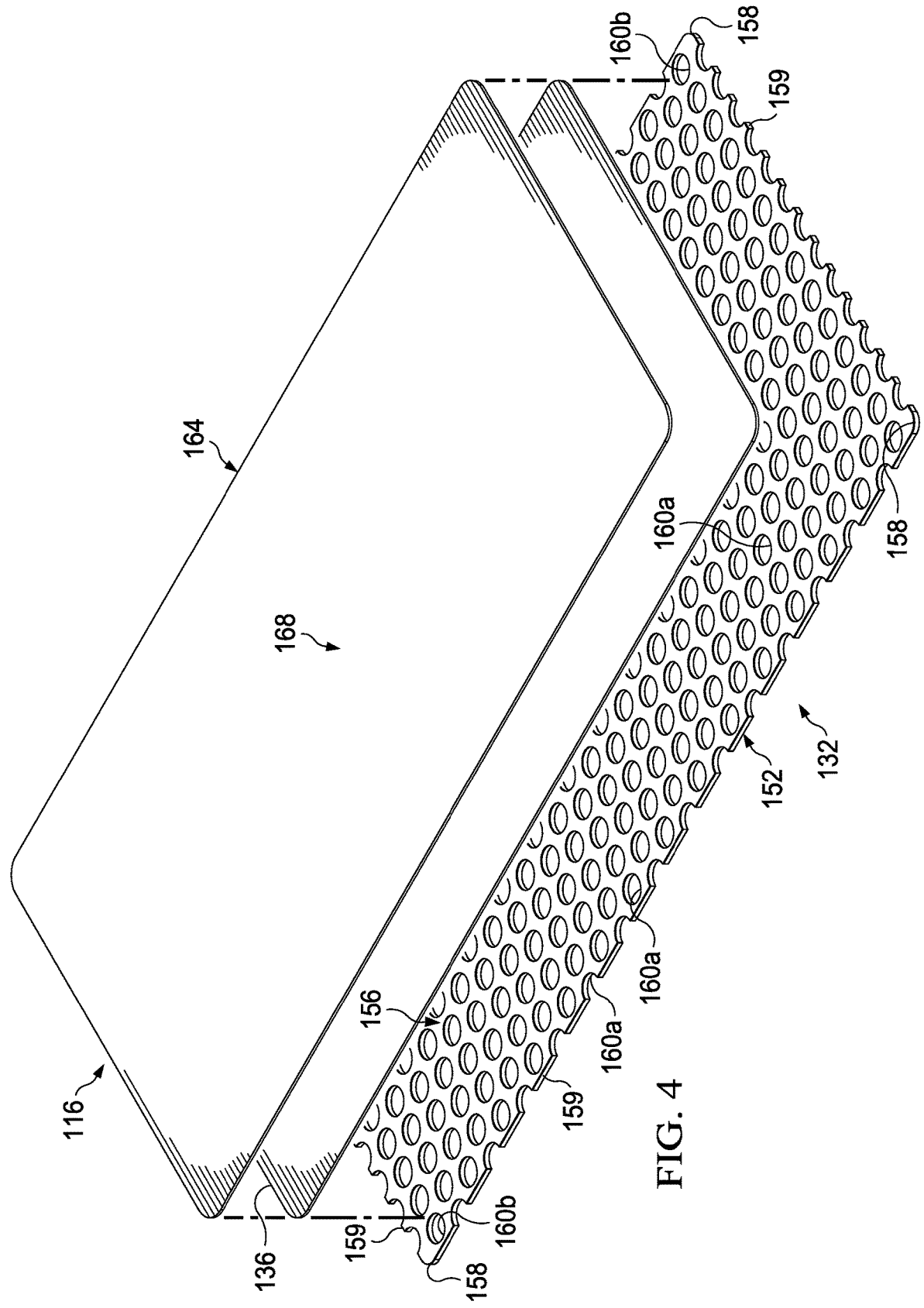

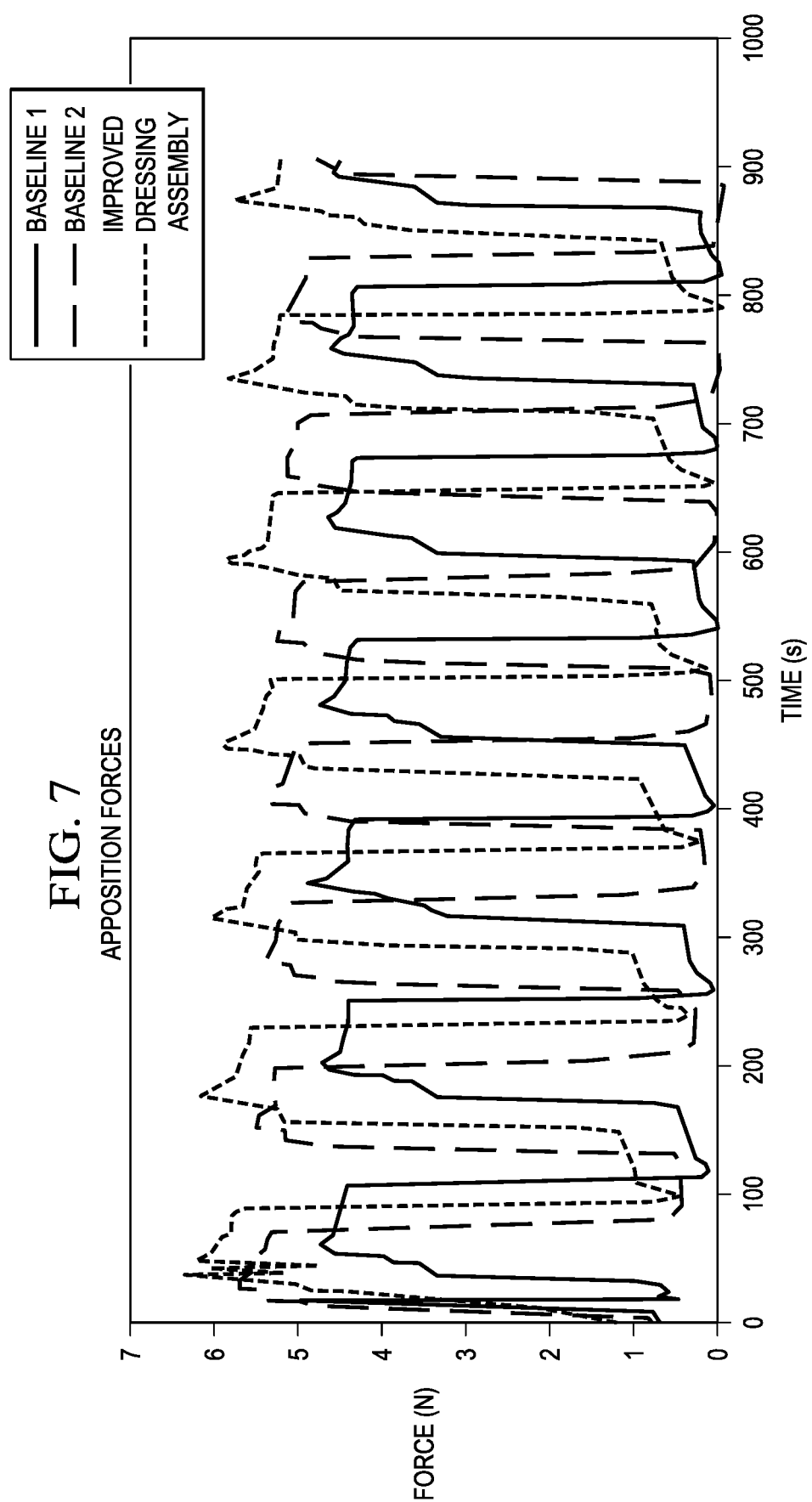

DRESSING WITH INCREASED APPOSITION FORCE

RELATED APPLICATION

This application claims the benefit, under 35 USC 119(e), of the filing of U.S. Provisional Patent Application No. 62/212,787, entitled "Dressing with Increased Apposition Force," filed Sep. 1, 2015, which is incorporated herein by reference for all purposes.

TECHNICAL FIELD

This disclosure relates generally to medical treatment systems and, more particularly, but not by way of limitation, to reduced pressure dressings, systems, and methods for treating a tissue site.

BACKGROUND

Clinical studies and practice have shown that reducing pressure in proximity to a tissue site can augment and accelerate growth of new tissue at the tissue site. The applications of this phenomenon are numerous, but have been proven particularly advantageous for treating wounds. Regardless of the etiology of a wound, whether trauma, surgery, or another cause, proper care of the wound is important to the outcome. Treatment of wounds or other tissue with reduced pressure may be commonly referred to as "reduced-pressure therapy." However, such treatment may also be known by other names including "negative-pressure therapy," "negative-pressure wound therapy," "vacuum therapy," "vacuum-assisted closure," and "topical negative-pressure," for example. Reduced-pressure therapy may provide a number of benefits, including migration of epithelial and subcutaneous tissues, improved blood flow, and micro-deformation of tissue at a tissue site. Together, these benefits can increase development of granulation tissue and reduce healing times.

Cost and complexity can limit the application of reduced-pressure therapy systems. Development and operation of therapy systems, components, and processes may benefit manufacturers, healthcare providers, and patients.

SUMMARY

In some illustrative embodiments, a system for treating a tissue site may include a dressing bolster, a comfort layer, an interface seal, a base layer, a sealing member, and a reduced-pressure source. The dressing bolster may include a first side, a second side, and a periphery. The comfort layer may include a first side and a second side. The first side of the comfort layer may be coupled to the second side of the dressing bolster. The interface seal may be coupled to the second side of the comfort layer. The base layer may include a base layer flange configured to be coupled to the dressing bolster and to extend beyond the periphery of the dressing bolster. The sealing member may be configured to cover the dressing bolster and to create a sealed space relative to the tissue site. The reduced-pressure source may be configured to be coupled in fluid communication with the sealed space.

In some illustrative embodiments, a dressing assembly may include a dressing bolster, an interface seal, a base layer, a sealing member, and an adhesive. The dressing bolster may include a first side, a second side, and a periphery. The interface seal may be coupled at the periphery of the dressing bolster. The base layer may include a base layer flange configured to be coupled to the dressing bolster and to extend beyond the periphery of the dressing bolster. The sealing member may be configured to cover at least a portion of the first side of the dressing bolster. The adhesive may be positioned at least between the sealing member and the base layer flange.

In some illustrative embodiments, a method for treating a tissue site may include providing a dressing bolster having a first side, a second side, and an edge defining an outer boundary of the dressing bolster. Further, the method may include positioning an interface seal between the second side of the dressing bolster and the tissue site at the edge of the dressing bolster. Further, the method may include coupling a base layer to the dressing bolster and to a tissue around the tissue site. Further, the method may include covering the first side of the dressing bolster with a sealing member to form a sealed space relative to the tissue site.

In some illustrative embodiments, a system for treating a tissue site may include a manifold, an interface seal, a base layer, and a drape. The manifold may include a first side, a second side, and a periphery. The interface seal may be positioned at the periphery of the manifold and on the second side of the manifold. The base layer may include a base layer flange configured to extend beyond the periphery of the manifold. The drape may be configured to cover the first side of the manifold and to create a sealed space relative to the tissue site.

In some illustrative embodiments, a dressing assembly may include a manifold, an interface seal, and a base layer. The manifold may include a first side, a second side, and a periphery. The interface seal may be coupled at the periphery of the manifold. The base layer may include a base layer flange configured to extend beyond the periphery of the manifold.

Other features and advantages of the illustrative embodiments will become apparent with reference to the drawings and detailed description that follow.

BRIEF DESCRIPTION OF THE DRAWINGS

FIG. 4 is an exploded view of an illustrative embodiment of a sealing member, an adhesive, and a base layer depicted in FIG. 3;

FIG. 7 is a graph illustrating an increase in apposition force generated by an improved dressing assembly and system according to this disclosure.

DETAILED DESCRIPTION OF ILLUSTRATIVE EMBODIMENTS

In the following detailed description of illustrative embodiments, reference is made to the accompanying drawings that form a part hereof. The illustrative embodiments are described in sufficient detail to enable those skilled in the art to practice the subject matter of this disclosure. Other embodiments may be utilized, and logical, structural, mechanical, electrical, and chemical changes may be made without departing from the scope of this disclosure. To avoid detail not necessary to enable those skilled in the art to practice the embodiments described herein, the description may omit certain information known to those skilled in the art. Therefore, the following detailed description is non-limiting, with the scope of the illustrative embodiments being defined by the appended claims.

Figure 1:
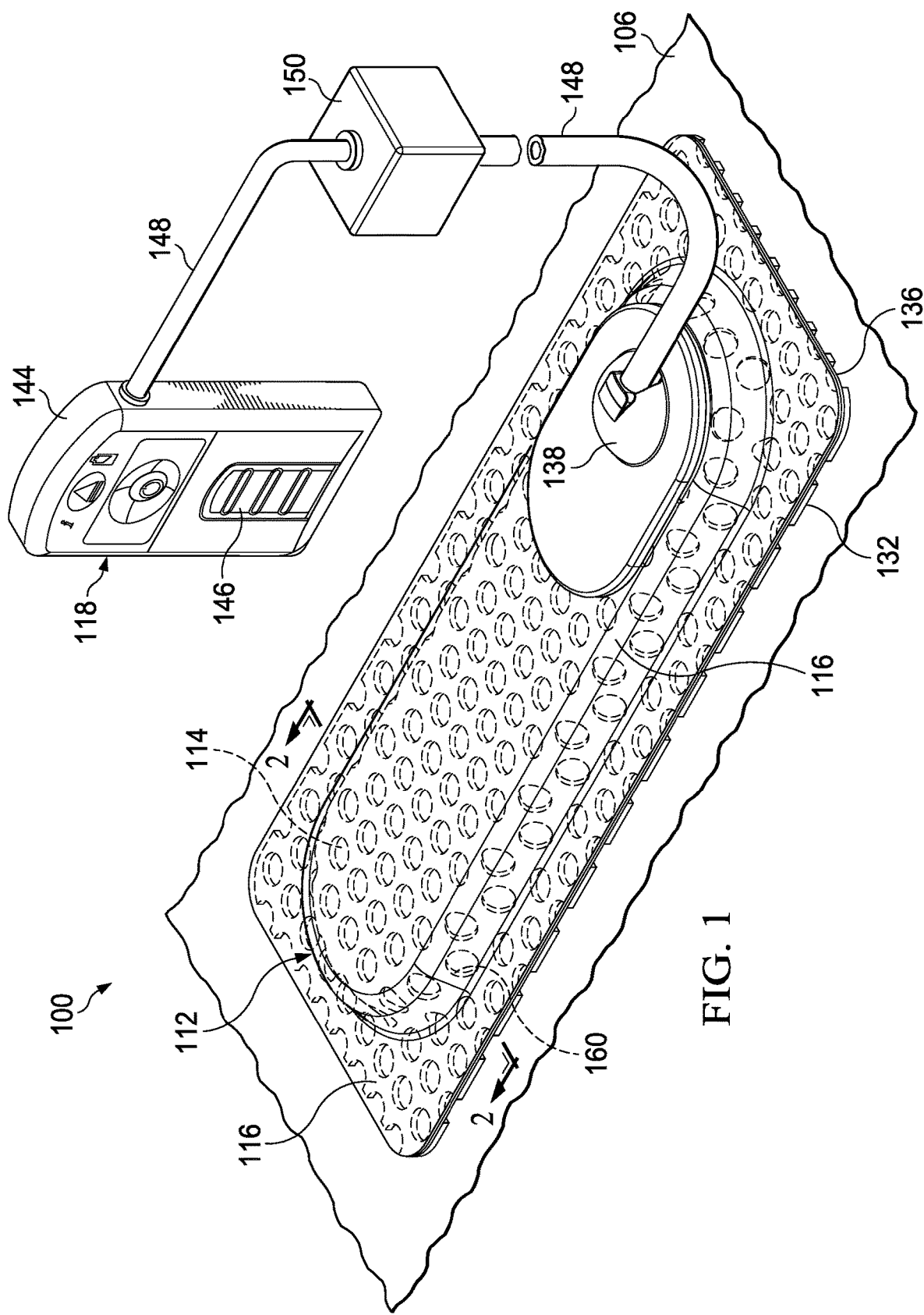
FIG. 1 is a perspective view of an illustrative embodiment of a system for treating a tissue site.
Figure 2:
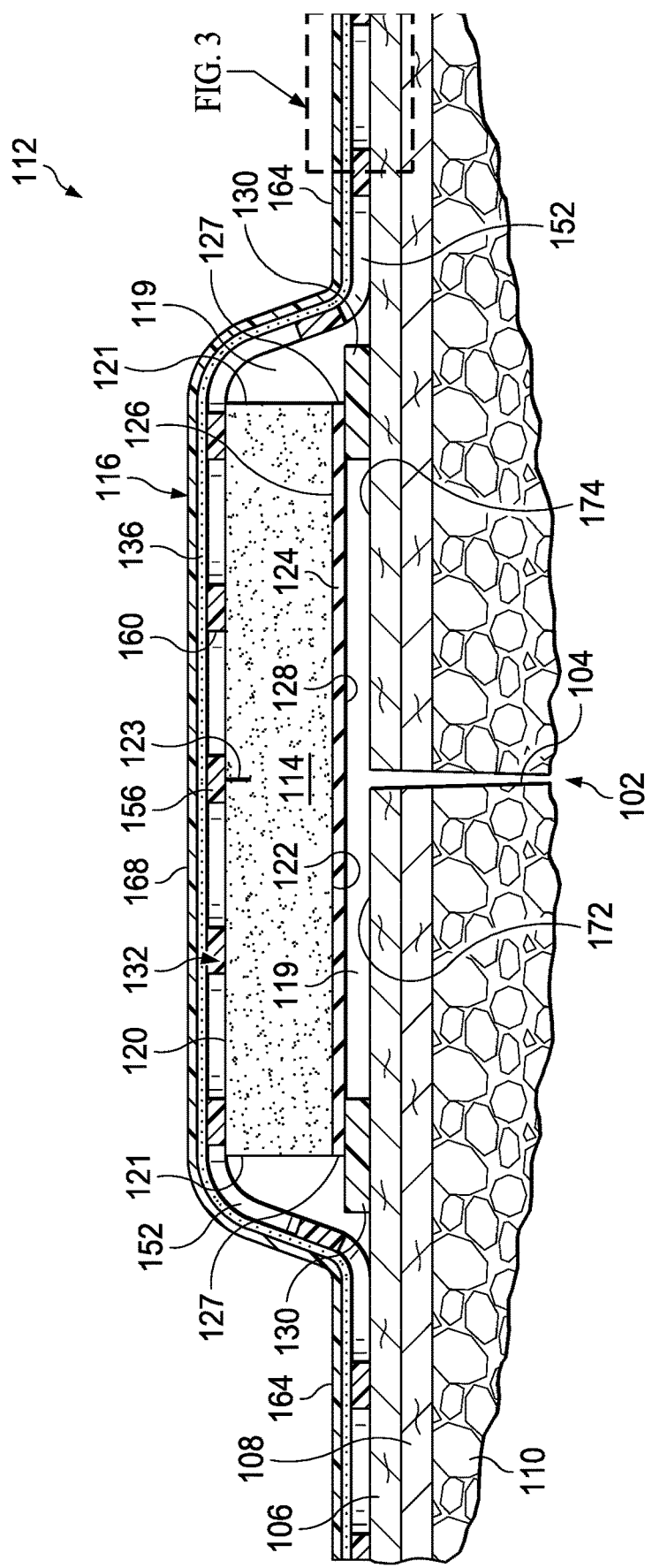
FIG. 2 is a cross-section of a portion of an illustrative embodiment of a dressing assembly depicted in FIG. 1, taken along line 2-2.

Referring to FIGS. 1 and 2, presented is an illustrative, non-limiting embodiment of a treatment system 100 for treating a tissue site 102, such as a linear wound or an incision 104. The incision 104 is shown extending through or involving an epidermis 106, a dermis 108, and a subcutaneous tissue 110. The treatment system 100 may also be used with other tissue sites, and may be used with or without reduced pressure.

The treatment system 100 may include a dressing assembly 112. The dressing assembly 112 may include, without limitation, a dressing bolster 114. In some embodiments, the dressing bolster 114 may be a manifold 114. Further, elements of the dressing bolster 114 may be applicable to the manifold 114, and the dressing bolster 114 may be interchangeably referred to herein as the manifold 114. In addition to the dressing assembly 112, the treatment system 100 may include a sealing member 116 and a reduced-pressure subsystem 118. While the treatment system 100 is shown in the context of a reduced-pressure dressing over an incision 104, the treatment system 100 may be used on other tissue sites, including open wounds.

In some embodiments, the sealing member 116 may be a drape 116, and the sealing member 116 or the drape 116 may form part of the dressing assembly 112. The sealing member 116 may be configured to cover the dressing bolster 114 and to create a sealed space 119 relative to the tissue site 102, for example, between the sealing member 116 and the tissue site 102. Further, the sealing member 116 may cover other tissue, such as a portion of the epidermis 106, around or surrounding the tissue site 102 to provide the sealed space 119 between the sealing member 116 and the tissue site 102. The dressing bolster 114 may be positioned in the sealed space 119.

The reduced-pressure subsystem 118 may include a reduced-pressure source 144. The reduced-pressure source 144 may provide reduced pressure as a part of the treatment system 100, and may be configured to be coupled in fluid communication with the sealed space 119. For example, the reduced-pressure source 144 may be fluidly coupled to a conduit interface 138 by a delivery conduit 148. An aperture (not shown) may be formed on a portion of the sealing member 116 to allow fluid communication between the sealed space 119 and the reduced-pressure sourced 144 through the conduit interface 138 and the delivery conduit 148.

As used herein, "reduced pressure" may refer to a pressure less than the ambient pressure at a tissue site being subjected to treatment, such as the tissue site 102. The reduced pressure may be less than the atmospheric pressure. The reduced pressure may also be less than a hydrostatic pressure at a tissue site. Unless otherwise indicated, quantitative values of pressure stated herein are gauge pressures.

The reduced pressure delivered to the sealed space 119 and the dressing bolster 114 may be constant or varied, patterned or random, and may be delivered continuously or intermittently. Although the terms "vacuum" and "negative pressure" may be used to describe the pressure applied to a tissue site, the actual pressure applied to the tissue site may be more than the pressure normally associated with a complete vacuum. Consistent with the use herein, unless otherwise indicated, an increase in reduced pressure or vacuum pressure may refer to a relative reduction in absolute pressure.

The reduced-pressure source 144 may include a reservoir region 146, or canister region. An interposed membrane filter (not shown), such as a hydrophobic or oleophobic filter, may be interspersed between the reduced-pressure delivery conduit 148 and the reduced-pressure source 144. One or more devices, such as a representative device 150, may be fluidly coupled to the reduced-pressure delivery conduit 148. The representative device 150 may be, for example, another fluid reservoir, a collection member to hold exudates and other fluids removed, a pressure-feedback device, a volume detection system, a blood detection system, an infection detection system, a flow monitoring system, or a temperature monitoring system. Multiple representative devices 150 may be included. One or more of the representative devices 150 may be formed integrally with the reduced-pressure source 144.

The reduced-pressure source 144 may be any device for supplying a reduced pressure, such as a vacuum pump, wall suction, or other source. While the amount and nature of reduced pressure applied to a tissue site may vary according to the application, the reduced pressure may be, for example, between about −5 mm Hg (−667 Pa) to about −500 mm Hg (−66.7 kPa). In some embodiments, the reduced pressure may be between about −75 mm Hg (−9.9 kPa) to about −300 mm Hg (−39.9 kPa).

The reduced pressure developed by the reduced-pressure source 144 may be delivered through the delivery conduit 148 to the conduit interface 138. The conduit interface 138 may allow the reduced pressure to be delivered through the sealing member 116 to the dressing bolster 114. In some embodiments, the conduit interface 138 may provide fluid communication external to the sealing member 116 without the application of reduced pressure.

The dressing bolster 114 may have a first side 120, a periphery 121, and a second, inward-facing side 122. The second, inward-facing side 122 of the dressing bolster 114 may be configured to face the tissue site 102. The first side 120 of the dressing bolster 114 may be opposite the second, inward-facing side 122 such that the first side 120 may be configured to face outward or away from the tissue site 102. The periphery 121 of the dressing bolster 114 may define an outer boundary or lateral boundary of the dressing bolster 114 and the first side 120 and the second, inward-facing side 122 of the dressing bolster 114.

In some embodiments, the periphery 121 of the dressing bolster 114 may be an edge 121 of the dressing bolster 114. The edge 121 of the dressing bolster 114 may be a lateral edge positioned orthogonal relative to the second, inward-facing side 122 of the dressing bolster 114. The edge 121 of the dressing bolster 114 may also be a beveled edge or an angled edge. The angled or beveled edge may help distribute shear stress between the dressing bolster 114 and the epidermis 106 of a patient.

In some embodiments, the dressing bolster 114 may include one or more notches, recesses, or cuts, such as a notch 123. For example, the notch 123 may be a lateral or longitudinal cut in the dressing bolster 114 on the first side 120. The notch 123 may enhance the flexibility of the dressing bolster 114. Enhanced flexibility may be particularly useful for application of the dressing assembly 112 over a joint or other area of movement on a patient. The notch 123 may also take various shapes without limitation, such as, for example, hexagons, slits, or squares.

The dressing bolster 114 may be formed from any bolster material or manifold material capable of providing a vacuum space, or treatment space. For example, the dressing bolster 114 may be formed from a porous and permeable foam or foam-like material, a member formed with pathways, a graft, a gauze, or any combination thereof. Reduced pressure applied to the dressing bolster 114 may enhance the permeability of the dressing bolster 114.

The term "manifold" as used herein may refer to a substance or structure that may assist in applying reduced pressure to, delivering fluids to, or removing fluids from a tissue site. A manifold may include a plurality of flow channels or pathways. The plurality of flow channels may be interconnected to improve distribution of fluids provided to and removed from an area of tissue around the manifold. Examples of manifolds may include, without limitation, devices that have structural elements arranged to form flow channels, cellular foam, such as open-cell foam, porous tissue collections, and liquids, gels, and foams that include or cure to include flow channels.

In some embodiments, the dressing bolster 114 may be a reticulated, open-cell polyurethane or polyether foam that may be fluid permeable. One such foam material may be a VAC® GranuFoam® material available from Kinetic Concepts, Inc. (KCI) of San Antonio, Tex. The reticulated pores of the GranuFoam® material may be helpful in carrying out the manifold function, but as stated above, other materials may be utilized. A material with a higher or lower density than the GranuFoam® material may be desirable in some embodiments. This material may have, for example, a smaller pore size than the GranuFoam® material. Among the many possible materials, the following may be used without limitation: GranuFoam® material, FXI technical foam (www.fxi.com), gauze, a flexible channel-containing member, a graft, and other similar materials. In some embodiments, ionic silver may be added to the material, such as, for example, by a micro bonding process. Other substances, such as antimicrobial agents, may also be added to the material.

In some embodiments, the dressing assembly 112 may include a comfort layer 124 having a first side 126, a periphery 127, and a second, inward-facing side 128. In some embodiments, the comfort layer 124 may be an interface layer 124. Further, elements of the comfort layer 124 may be applicable to the interface layer 124, and the comfort layer 124 may be interchangeably referred to herein as the interface layer 124.

The second, inward-facing side 128 of the comfort layer 124 may be configured to face the tissue site 102. The first side 126 of the comfort layer 124 may be opposite the second, inward-facing side 128 such that the first side 126 may be configured to face outward or away from the tissue site 102. The periphery 127 of the comfort layer 124 may define an outer boundary or lateral boundary of the comfort layer 124 and the first side 126 and the second, inward-facing side 128 of the comfort layer 124. In some embodiments, the periphery 127 of the comfort layer 124 may be an edge 127 of the comfort layer 124.

The first side 126 of the comfort layer 124 may be coupled, for example, by a heat bond or other suitable technique to the second, inward-facing side 122 of the dressing bolster 114. In some embodiments, the periphery 127 of the comfort layer 124 may substantially correspond to, or be substantially aligned with, the periphery 121 of the dressing bolster 114. The comfort layer 124 may enhance patient comfort when the dressing bolster 114 is adjacent to the epidermis 106 of a patient. For example, in some embodiments, at least a portion of the second, inward-facing side 128 of the comfort layer 124 may be configured to directly contact the tissue site 102.

The comfort layer 124 may be any material suitable for preventing skin irritation and discomfort while allowing fluid transmission through the comfort layer 124. As non-limiting examples, a woven material, an elastic material, a polyester knit textile substrate, a non-woven material, or a fenestrated film may be used. As another non-limiting example, an InterDry™ textile material from Milliken Chemical, a division of Milliken & Company, Inc. of Spartanburg, S.C., may be used. In some embodiments, the comfort layer 124 may include antimicrobial substances, such as silver.

In some embodiments, the dressing assembly 112 may include an interface seal 130. In some embodiments, the interface seal 130 may be a sealing ring 130. Further, elements of the interface seal 130 may be applicable to the sealing ring 130, and the interface seal 130 may be interchangeably referred to herein as the sealing ring 130. The interface seal 130 may enhance or otherwise provide a fluid seal at or around the tissue site 102, such as the incision 104. For example, a surface of the epidermis 106 may have recesses, cracks, wrinkles, or other discontinuities that may cause leaks. Moreover, folds, buckles, wrinkles, or other discontinuities may form in the sealing member 116 that can cause leaks. The interface seal 130 may help seal any such skin or sealing member discontinuities at or around the tissue site 102. Further, the interface seal 130 may also enhance the ability of the dressing assembly 112 to impart an apposition force to the tissue site 102, for example, for closing the incision 104, or otherwise moving portions of tissue toward one another at the tissue site 102.

The interface seal 130 may function as a two-sided gasket that may provide a seal between the dressing assembly 112 and the tissue site 102 and/or epidermis 106. For example, the interface seal 130 may provide a seal between the dressing bolster 114, the comfort layer 124, or the sealing member 116 and the tissue site 102 and/or epidermis 106. The interface seal 130 may also absorb perspiration or other fluids from the tissue site 102. Further, the interface seal 130 may distribute shear forces created, for example, by the application of reduced pressure at the interface of the dressing bolster 114 and the tissue site 102 and/or the epidermis 106.

The interface seal 130 may be adapted to be positioned between the dressing bolster 114 and the tissue site 102. For example, the interface seal 130 may be positioned between the second, inward-facing side 122 of the dressing bolster 114 and the tissue site 102. In some embodiments, the interface seal 130 may be coupled to the second, inward-facing side 122 of the dressing bolster 114.

In some embodiments, the interface seal 130 may be positioned at the periphery 121 of the dressing bolster 114, or coupled to the periphery 121 of the dressing bolster 114. Further, the interface seal 130 may be positioned between the dressing bolster 114 and tissue at or around the tissue site 102, such as the epidermis 106. Thus, in some embodiments, at least a portion of the interface seal 130 may be positioned around the periphery 121 of the dressing bolster 114 and a periphery of the tissue site 102. Further, in some embodiments, at least a portion of the interface seal 130 may substantially surround the periphery 121 of the dressing bolster 114 and a periphery of the tissue site 102.

In some embodiments, other layers or elements, such as the comfort layer 124, may be included with the dressing assembly 112 and positioned between the dressing bolster 114 and the interface seal 130. In such embodiments, at least a portion of the second, inward facing side 122 of the dressing bolster 114 and/or the second, inward-facing side 128 of the comfort layer 124 may be free of the interface seal 130 and configured to be positioned in fluid communication with the tissue site 102.

The interface seal 130 may be formed, as an illustrative example, by applying or bonding sealing material to the dressing bolster 114. The sealing material that may be used for the interface seal 130 may include hydrocolloids, hydrogels, silicone polymers (both crosslinked and uncrosslinked gels), and natural gums (xanthan, guar, cellulose). The sealing material may include other soft polymer gels, such as, for example, those based on polyurethanes, polyolefin gels, and acrylics.

The interface seal 130 may have a durometer, such as a material softness or hardness, between about 20 Shore 00 to about 90 Shore OO. In some embodiments, the durometer of the interface seal 130 may be between about 70 Shore 00 to about 80 Shore OO. Further, the interface seal 130 may have a modulus of elasticity that falls between a modulus of elasticity of the sealing member 116 and a modulus of elasticity of the tissue site 102 and/or the epidermis 106.

The interface seal 130 may have a width between about 10 millimeters to about 30 millimeters. In some embodiments, the width of the interface seal 130 may be about 20 millimeters. The width of the interface seal 130 may be directed, oriented, or adapted for positioning along a surface of the tissue site 102. In some embodiments, the width of the interface seal 130 may extend beyond the edge 121 of the dressing bolster 114 by about 10 millimeters and also overlap the second, inward-facing side 122 of the dressing bolster 114 by about 10 millimeters. Thus, the interface seal 130 may straddle the edge or periphery 121 of the dressing bolster 114, or otherwise extend beyond the periphery 121 of the dressing bolster 114. In other embodiments (not shown), the dressing bolster 114 may entirely overlap the interface seal 130.

The interface seal 130 may have a thickness between about 0.3 millimeters to about 2.5 millimeters. In some embodiments, the thickness of the interface seal 130 may be between about 0.7 millimeters to about 1.25 millimeters. The thickness of the interface seal 130 may be perpendicular to the width of the interface seal 130 and the tissue site 102. Other dimensions for the interface seal 130 are possible.

The interface seal 130 may be deployed by hand or extruded from an applicator, such as a syringe, prior to application of the dressing assembly 112 to the tissue site 102. Sealing materials suitable for application by extrusion may include water soluble gums such as xanthan, guar, or cellulose, and thick greases, such as silicones. In other embodiments, the interface seal 130 may be bonded in any suitable manner, such as, for example, by a heat bond, to the dressing assembly 112 during manufacture. In some embodiments, the interface seal 130 may have a ring-like or annular shape. In other embodiments, the interface seal 130 may be linear. Further, in some embodiments, the interface seal 130 may comprise one or more discrete members, including linear members, which may be formed into a ring-like or annular shape.

The interface seal 130 may be coupled directly to the dressing assembly 112, or coupled with an attachment device, such as an acrylic adhesive, cement, or other coupling device. In some embodiments, the interface seal 130 may be coupled to the second inward-facing side 122 of the dressing bolster 114, and/or to an adjacent layer, such as the second, inward facing side 128 of the comfort layer 124. Further, in some embodiments, the interface seal 130 may be adapted to be positioned between the comfort layer 124 and the tissue site 102, and/or tissue around the tissue site 102, such as the epidermis 106. Thus, in some embodiments, the comfort layer 124 may be coupled between the dressing bolster 114 and the interface seal 130.

In some embodiments, the interface seal 130 may include an absorbent. For example, the interface seal 130 may be a hydrocolloid comprising an absorbent, such as carboxy methyl cellulose (CMC). The absorbent may permit the interface seal 130 to absorb fluid from the tissue site 102 in addition to enhancing the fluid seal around the tissue site 102. The interface seal 130 including the absorbent may enhance the ability of the dressing assembly 112 to manage and direct fluid away from the tissue site 102 for keeping the tissue site 102 dry. For example, the dressing bolster 114 may have a thickness between the first side 120 and the second, inward-facing side 122 of the dressing bolster 114. The thickness of the dressing bolster 114 may define at least a portion of a thickness of the dressing assembly 112. The interface seal 130 may be adapted to be positioned between the dressing assembly 112 and the tissue site 102, as described above, and around or surrounding a circumference, perimeter, or periphery of the tissue site 102.

Relative to the dressing assembly 112, the interface seal 130 may be positioned, for example, around, on, or at the edge or periphery 121 of the dressing bolster 114 and/or the comfort layer 124. Further, the interface seal 130 may be positioned around or surrounding a circumference of the dressing bolster 114 and/or the comfort layer 124. Further, the interface seal 130 may be positioned around at least a portion of the dressing bolster 114 or the comfort layer 124 that is configured to be positioned directly against or in direct contact with the tissue site 102. At least a portion of the dressing bolster 114 and/or the comfort layer 124 may be exposed and configured to be positioned directly against the tissue site 102 when the interface seal 130 is positioned on the dressing assembly 112. Further, in such embodiments, the interface seal 130 may surround the exposed portion of the dressing bolster 114 and/or the comfort layer 124.

The absorbent in the interface seal 130 may wick or draw fluid in a lateral direction within the dressing assembly 112, normal to the thickness of the dressing bolster 114, and toward the edge or periphery 121 of the dressing bolster 114 for absorption in the interface seal 130. Thus, fluid from the tissue site 102 may be wicked or otherwise drawn in a lateral direction along the surface of the tissue site 102 toward the edge or periphery 121 of the dressing bolster 114 and into the interface seal 130. Further, fluid from the tissue site 102 may also flow through the thickness of the dressing assembly 112 and the dressing bolster 114 at least by operation of the manifold material comprising the dressing bolster 114, described above.

Figure 3:
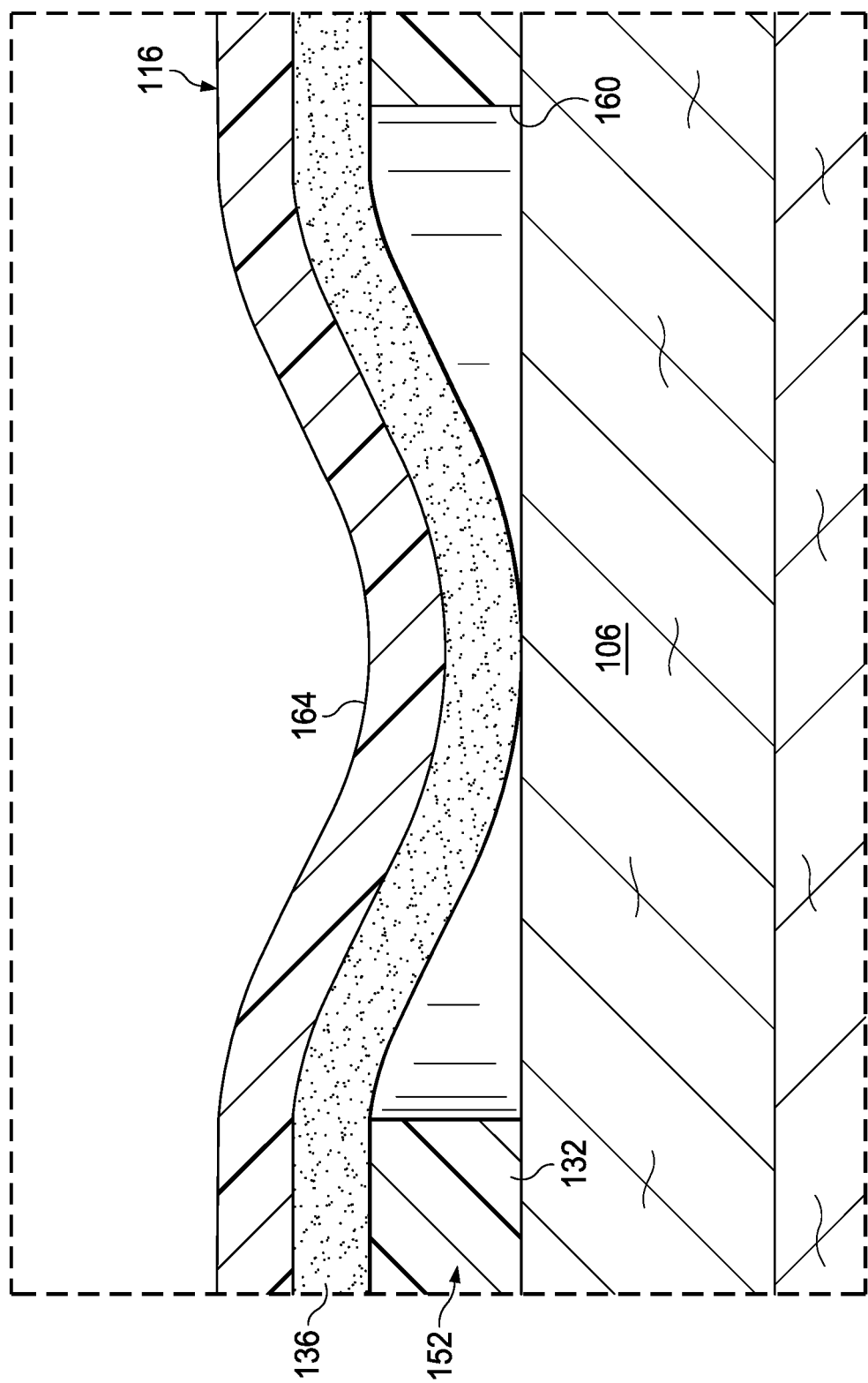
FIG. 3 is a detail view, taken at reference FIG. 3 shown in FIG. 2, illustrating the dressing assembly of FIG. 1 positioned proximate to tissue surrounding the tissue site.

Referring to FIGS. 2-4, in some embodiments, the dressing assembly 112 may include a base layer 132. The use and configuration of the base layer 132 in the dressing assembly 112 may be beneficial for reducing the formation, size, and appearance of scars by, for example, increasing temperature and hydration levels at the tissue site 102. The base layer 132 may also enhance the ability of the dressing assembly 112 to impart apposition force to the tissue site 102, for example, for closing the incision 104 or otherwise contracting a portion of the tissue site 102. The base layer 132 may be configured to be coupled to the dressing bolster 114 and/or tissue around the tissue site 102 with an attachment device, such as an adhesive 136. In some embodiments, a portion of the base layer 132 may be configured to be coupled to the first side 120 of the dressing bolster 114.

The base layer 132 may include a base layer flange 152 configured to extend beyond the periphery 121 of the dressing bolster 114, for example, for coupling to tissue around or surrounding the tissue site 102. In some embodiments, the base layer flange 152 may be configured to be positioned in direct contact with tissue around or surrounding the tissue site 102, such as the epidermis 106. Further, the base layer flange 152 may be positioned around or surrounding a central region 156 of the base layer 132. Thus, in some embodiments, the base layer flange 152 may define, form, or be positioned at, a periphery of the base layer 132. Further, the base layer flange 152 may be configured to be positioned around the periphery 121 of the dressing bolster 114. In some embodiments, the base layer flange 152 may be configured to substantially or entirely surround the periphery 121 of the dressing bolster 114.

The base layer 132 may include corners 158 and edges 159. The corners 158 and the edges 159 may be part of the base layer flange 152. One of the edges 159 may meet another of the edges 159 to define one of the corners 158. Further, the base layer 132 may include a plurality of apertures 160 disposed through the base layer 132. In some embodiments, the apertures 160 may be disposed through the central region 156 of the base layer 132, for example, to facilitate fluid communication with the dressing bolster 114 and/or to couple the base layer 132 to the dressing bolster 114. In some embodiments, the apertures 160 may be disposed through the base layer flange 152, for example, to facilitate coupling the base layer 132 to tissue around or surrounding the tissue site 102 as described below.

The central region 156 of the base layer 132 may be positioned adjacent to or proximate to the dressing bolster 114, and the base layer flange 152 may be positioned adjacent to or proximate to tissue surrounding the tissue site 102. In this manner, the base layer flange 152 may be positioned around or surrounding the dressing bolster 114. Further, the apertures 160 in the base layer 132 may be in fluid communication with the dressing bolster 114 and tissue around or surrounding the tissue site 102.

The apertures 160 in the base layer 132 may have any shape, such as, for example, circles, squares, stars, ovals, polygons, slits, complex curves, rectilinear shapes, triangles, or other shapes. The apertures 160 may be formed by cutting, by application of local RF energy, or other suitable techniques for forming an opening. Each of the apertures 160 of the plurality of apertures 160 may be substantially circular in shape, having a diameter and an area. The area of each of the apertures 160 may refer to an open space or open area defining each of the apertures 160. The diameter of each of the apertures 160 may define the area of each of the apertures 160. The area of the apertures 160 described in the illustrative embodiments herein may be substantially similar to the area in other embodiments (not shown) for the apertures 160 that may have non-circular shapes.

The diameter of each of the apertures 160 may be substantially the same, or each of the diameters may vary depending, for example, on the position of the aperture 160 in the base layer 132. For example, the diameter of the apertures 160 in the base layer flange 152 may be larger than the diameter of the apertures 160 in the central region 156 of the base layer 132. The diameter of each of the apertures 160 may be between about 1 millimeter to about 50 millimeters. In some embodiments, the diameter of each of the apertures 160 may be between about 1 millimeter to about 20 millimeters. The apertures 160 may have a uniform pattern or may be randomly distributed on the base layer 132. Further, in some embodiments, an aperture 160b positioned at the corners 158 may be smaller than an aperture 160a positioned in the central region 156. In some embodiments, the apertures 160a may have a diameter between about 9.8 millimeters to about 10.2 millimeters, and the apertures 160b may have a diameter between about 7.75 millimeters to about 8.75 millimeters.

The base layer 132 may be a soft, pliable material. For example, the base layer 132 may comprise a silicone gel, a soft silicone, hydrocolloid, hydrogel, polyurethane gel, polyolefin gel, hydrogenated styrenic copolymer gels, a foamed gel, a soft closed cell foam such as polyurethanes and polyolefins coated with an adhesive described below, polyurethane, polyolefin, or hydrogenated styrenic copolymers. The base layer 132 may have a thickness between about 500 microns (μm) and about 1000 microns (μm). In some embodiments, the base layer 132 may have a stiffness between about 5 Shore OO to about 80 Shore OO. The base layer 132 may be comprised of hydrophobic or hydrophilic materials. The base layer 132 may be operable to transmit forces, such as, for example, an apposition force, proximate to the tissue site 102, and to enhance a fluid seal with the tissue site 102 as described herein.

In some embodiments (not shown), the base layer 132 may be a hydrophobic-coated material. For example, the base layer 132 may be formed by coating a spaced material, such as, for example, woven, nonwoven, molded, or extruded mesh with a hydrophobic material. The hydrophobic material for the coating may be a soft silicone, for example. In this manner, the spaced material may provide openings analogous to the apertures 160 described above.

The adhesive 136 may be in fluid communication with the apertures 160 in at least the base layer flange 152. In this manner, the adhesive 136 may be in fluid communication with tissue surrounding the tissue site 102 through the apertures 160 in the base layer 132. As described below and shown in FIG. 3, the adhesive 136 may extend or be pressed through the plurality of apertures 160 to contact the epidermis 106 for securing the dressing assembly 112 to, for example, tissue surrounding the tissue site 102. The apertures 160 may provide sufficient contact of the adhesive 136 to the epidermis 106 to secure the dressing assembly 112 about the tissue site 102. However, the configuration of the apertures 160 and the adhesive 136, described below, may permit release and repositioning of the dressing assembly 112 about the tissue site 102.

Referring to FIG. 4, at least one of the apertures 160a in the base layer flange 152 may be positioned at the edges 159 and may have an interior cut open or exposed at the edges 159 and in fluid communication in a lateral direction with an exterior of the edges 159. The lateral direction may refer to a direction in the same plane as the base layer 132. Thus, the exposed interior of the apertures 160a at the edges 159 may permit the adhesive 136 to flow around and exterior to the edges 159 for enhancing the adhesion of the edges 159 around the tissue site 102.

The size and configuration of the apertures 160 may be designed to control the adherence of the dressing assembly 112 at the tissue site 102. For example, the size and number of the apertures 160b in the corners 158 may be adjusted as necessary, depending on the chosen geometry of the corners 158, to maximize the exposed surface area of the adhesive 136. Further, the apertures 160b at the corners 158 may be fully housed within the base layer 132, substantially precluding fluid communication in a lateral direction exterior to the corners 158. The apertures 160b at the corners 158 being fully housed within the base layer 132 may substantially preclude fluid communication of the adhesive 136 exterior to the corners 159, and may provide improved handling of the dressing 124 during deployment at the tissue site 102. Further, the exterior of the corners 158 being substantially free of the adhesive 136 may increase the flexibility of the corners 158 to enhance comfort. Similar to the apertures 160b in the corners 158, any of the apertures 160 may be adjusted in size and number to maximize the surface area of the adhesive 136 in fluid communication through the apertures 160 for a particular application or geometry of the base layer 132.

The adhesive 136 may be a medically-acceptable adhesive. The adhesive 136 may also be flowable. For example, the adhesive 136 may comprise an acrylic adhesive, rubber adhesive, high-tack silicone adhesive, polyurethane, or other adhesive substance. In some embodiments, the adhesive 136 may be a pressure-sensitive adhesive comprising an acrylic adhesive with coating weight of 15 grams/m$^2$ (gsm) to 70 grams/m$^2$ (gsm). In some embodiments, the adhesive 136 may be a layer having substantially the same shape as the base layer 132. In some embodiments, the adhesive 136 may be continuous layer. In other embodiments, the adhesive 136 may be discontinuous. For example, the adhesive 136 may be a patterned coating on a carrier layer, such as, for example, a side of the sealing member 116 adapted to face the epidermis 106. Further, discontinuities in the adhesive 136 may be sized to control the amount of the adhesive 136 extending through the apertures 160 in the base layer 132 to reach the epidermis 106. The discontinuities in the adhesive 136 may also be sized to enhance the Moisture Vapor Transfer Rate (MVTR) of the dressing assembly 112.

Factors that may be utilized to control the adhesion strength of the dressing assembly 112 may include the diameter and number of the apertures 160 in the base layer 132, the thickness of the base layer 132, the thickness and amount of the adhesive 136, and the tackiness of the adhesive 136. An increase in the amount of the adhesive 136 extending through the apertures 160 may correspond to an increase in the adhesion strength of the dressing assembly 112. A decrease in the thickness of the base layer 132 may correspond to an increase in the amount of adhesive 136 extending through the apertures 160. Thus, the diameter and configuration of the apertures 160, the thickness of the base layer 132, and the amount and tackiness of the adhesive 136 utilized may be varied to provide a desired adhesion strength for the dressing assembly 112. In some embodiments, the thickness of the base layer 132 may be about 200 microns, the adhesive 136 may have a thickness of about 30 microns and a tackiness of 2000 grams per 25 centimeter wide strip, and the diameter of the apertures 160a in the base layer 132 may be about 10 millimeters.

In some embodiments, the tackiness of the adhesive 136 may vary in different locations of the base layer 132. For example, in locations of the base layer 132 where the apertures 160 are comparatively large, such as the apertures 160a, the adhesive 136 may have a lower tackiness than other locations of the base layer 132 where the apertures 160 are smaller, such as the apertures 160b. In this manner, locations of the base layer 132 having larger apertures 160 and lower tackiness adhesive 136 may have an adhesion strength comparable to locations having smaller apertures 160 and higher tackiness adhesive 136.

The sealing member 116 may have a periphery 164 and a central region 168. The periphery 164 of the sealing member 116 may be positioned proximate to the base layer flange 152. The adhesive 136 may be positioned at least between the periphery 164 of the sealing member 116 and the base layer flange 152. In some embodiments, a portion of the periphery 164 of the sealing member 116 may extend beyond the base layer flange 152 and into direct contact with tissue surrounding the tissue site 102. Thus, the adhesive 136 may also be positioned at least between the periphery 164 of the sealing member 116 and tissue, such as the epidermis 106, surrounding the tissue site 102. In some embodiments, the adhesive 136 may be disposed on a surface of the sealing member 116 adapted to face the tissue site 102 and the base layer 132.

In some embodiments, the sealing member 116 may be configured to extend beyond the periphery 121 of the dressing bolster 114. Further, in some embodiments, the sealing member 116 may be configured to cover at least a portion of the first side 120 of the dressing bolster 114 and to extend beyond the periphery 121 of the dressing bolster 114 proximate to the base layer flange 152. In some embodiments, the adhesive 136 may be positioned between the sealing member 116 and the base layer 132 such that the adhesive 136 is in fluid communication with at least the apertures 160 in the base layer flange 152. Thus, the adhesive 136 may be positioned at least between the sealing member 116 and the base layer flange 152. Further, in some embodiments, the adhesive 136 may be configured to be in fluid communication with tissue around or surrounding the tissue site 102 through the apertures 160 in the base layer flange 152.

The sealing member 116 may be formed from any material that allows for a fluid seal. A fluid seal may be a seal adequate to maintain reduced pressure at a desired site given the particular reduced pressure source or system involved. The sealing member 116 may comprise, for example, one or more of the following materials: hydrophilic polyurethane; cellulosics; hydrophilic polyamides; polyvinyl alcohol; polyvinyl pyrrolidone; hydrophilic acrylics; hydrophilic silicone elastomers; an INSPIRE 2301 material from Expopack Advanced Coatings of Wrexham, United Kingdom having, for example, an MVTR (inverted cup technique) of 14400 g/m$^2$/24 hours and a thickness of about 30 microns; a thin, uncoated polymer drape; natural rubbers; polyisoprene; styrene butadiene rubber; chloroprene rubber; polybutadiene; nitrile rubber; butyl rubber; ethylene propylene rubber; ethylene propylene diene monomer; chlorosulfonated polyethylene; polysulfide rubber; polyurethane (PU); EVA film; co-polyester; silicones; a silicone drape; a 3M Tegaderm® drape; a polyurethane (PU) drape such as one available from Avery Dennison Corporation of Pasadena, Calif.; polyether block polyamide copolymer (PEBAX), for example, from Arkema, France; Expopack 2327; or other appropriate material.

The sealing member 116 may be vapor permeable and liquid impermeable, thereby allowing vapor and inhibiting liquids from exiting the sealed space 119. In some embodiments, the sealing member 116 may be a flexible, breathable film, membrane, or sheet having a high moisture vapor transfer rate (MVTR) of, for example, at least about 300 g/m$^2$ per 24 hours. In other embodiments, a low or no vapor transfer drape might be used. The sealing member 116 may comprise a range of medically suitable films having a thickness between about 15 microns (µm) to about 50 microns (µm).

Figure 5A:
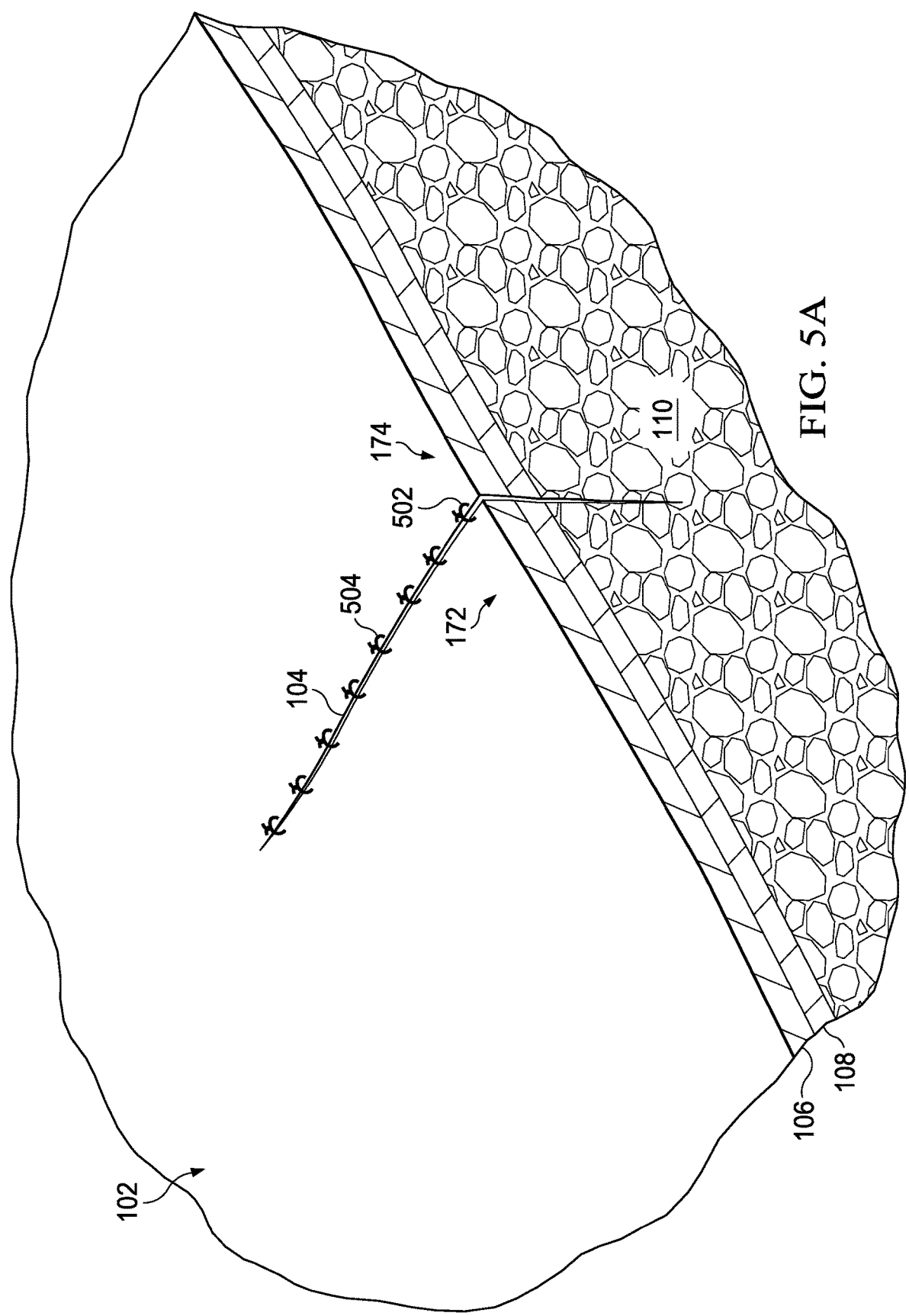
FIGS. 5A-5C are perspective, cross-sectional views of a portion of an illustrative embodiment of a system for treating a tissue site being deployed at the tissue site.
Figure 5B:
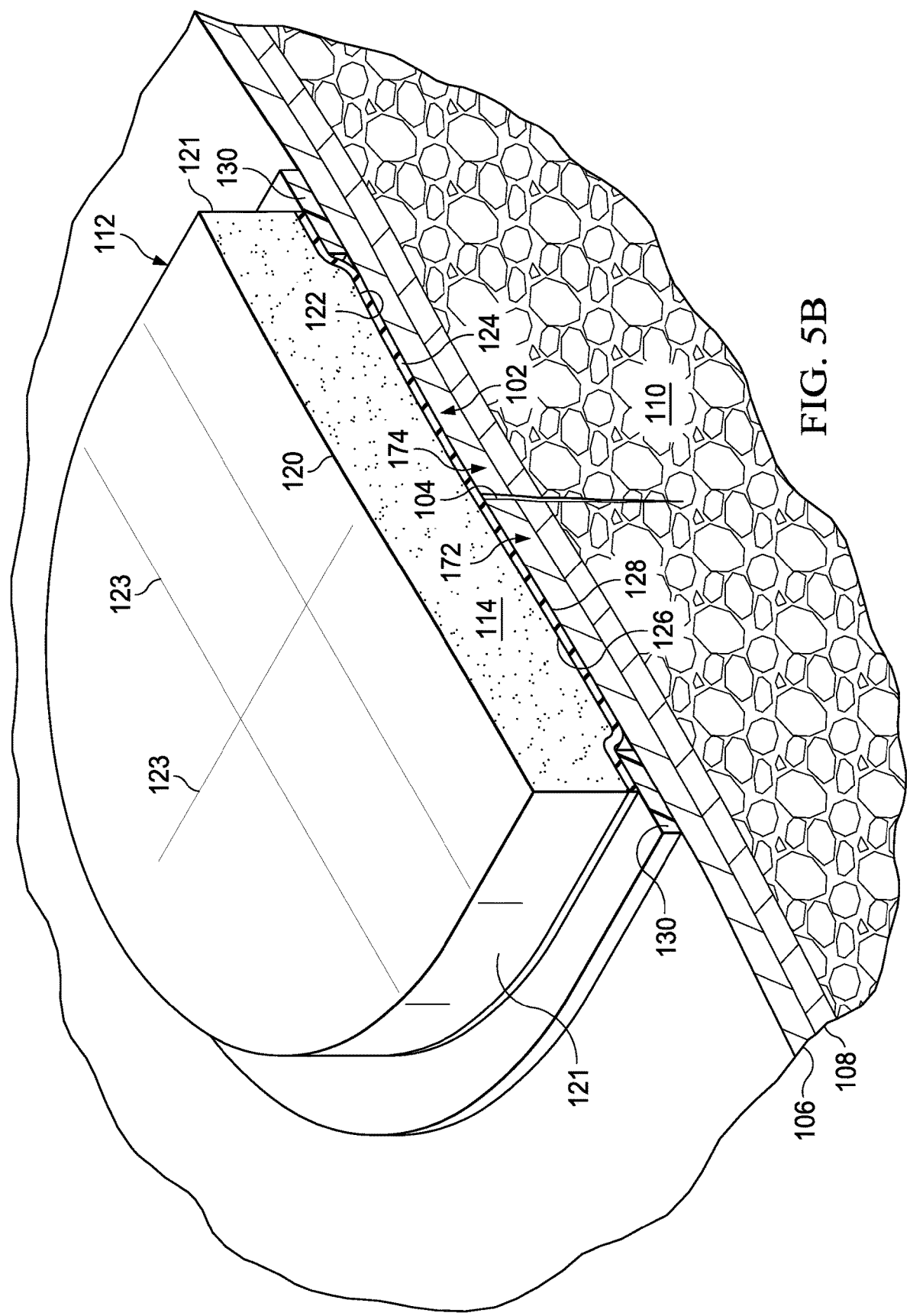
Figure 5C:
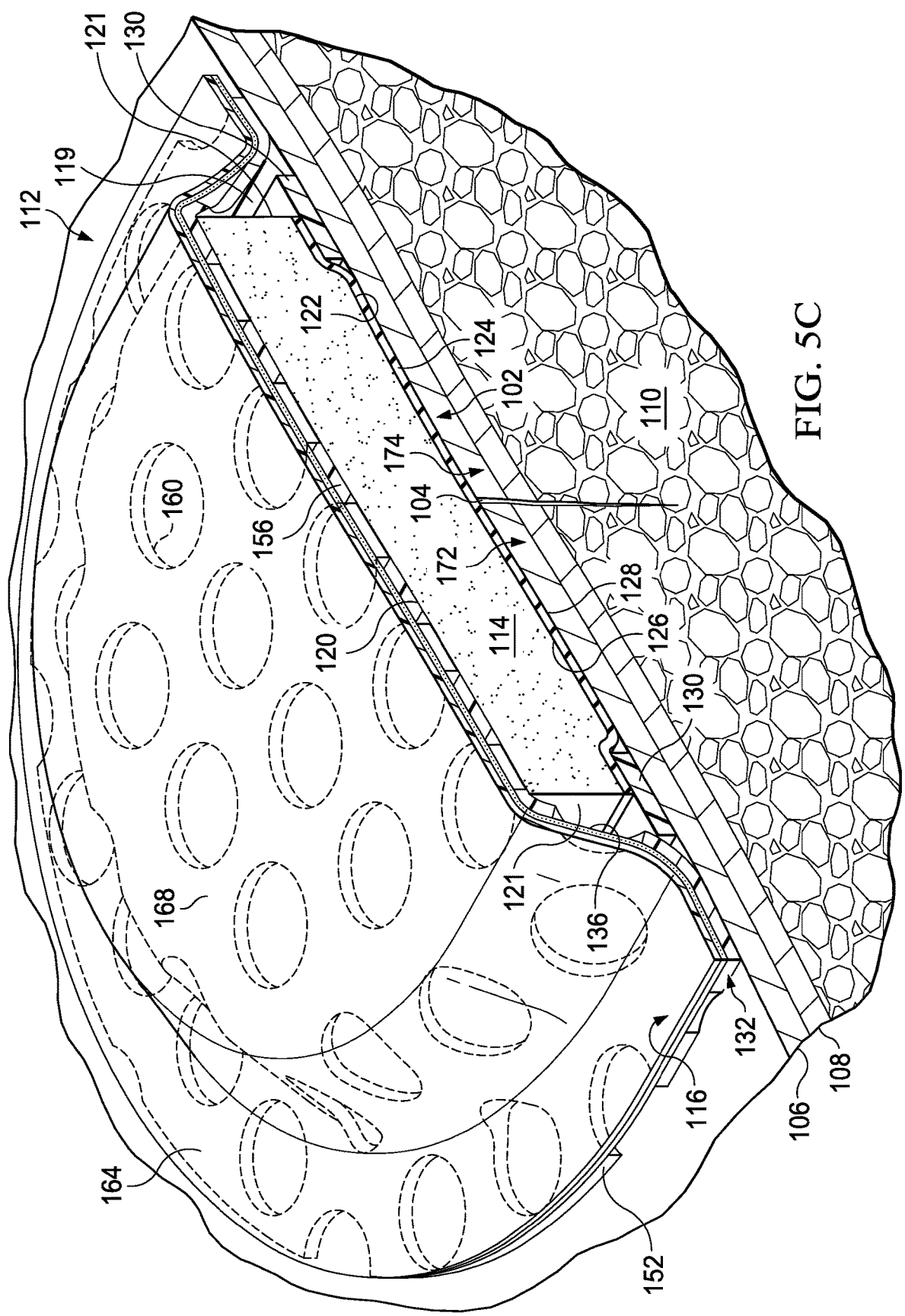

FIGS. 5A-5C provide an illustrative embodiment of a method for assembling the dressing assembly 112 in stages at the tissue site 102, such as the incision 104. In FIG. 5A, a closure device 502, such as, for example, stitches 504, may close the incision 104. Other closure devices 502, such as epoxy or staples may be utilized to close the incision 104. The tissue site 102 may include a first portion 172 and second portion 174. The first portion 172 of the tissue site 102 may be positioned on an opposite side of the incision 104 from the second portion 174 of the tissue site 102.

Referring to FIG. 5B, after the incision 104 is closed or prepared as described above, the dressing assembly 112 may be disposed proximate to the incision 104. For example, the dressing bolster 114 of the dressing assembly 112 may be positioned across the incision 104 between the first portion 172 and the second portion 174 of the tissue site 102. The comfort layer 124 may be positioned in contact with the tissue site 102 between the dressing bolster 114 and the tissue site 102. The dressing bolster 114 may be in fluid communication with the tissue site 102 through the comfort layer 124. The interface seal 130 may be positioned at the periphery 121 of the dressing bolster 114 and between the dressing bolster 114 and the tissue site 102. The interface seal 130 may be positioned around a portion of the comfort layer 124 positioned in direct contact with the tissue site 102. The portion of the comfort layer 124 in direct contact with the tissue site may be free of the interface seal 130 such that fluid communication is permitted through the comfort layer 124 to the dressing bolster 114. In other embodiments, elements may be added or omitted as desired. For example, in some embodiments, the comfort layer 124 may be omitted and the dressing bolster 114 may be positioned at the tissue site 102 as described for the comfort layer 124.

Referring to FIG. 5C, the sealing member 116 may be disposed over or covering the dressing bolster 114 and a portion of the epidermis 106 to form the sealed space 119 between the sealing member 116 and the incision 104. The sealing member 116, the base layer 132, and the adhesive 136 may be deployed together at the tissue site 102 as an assembly or kit. Once in position, the adhesive 136 may be pressed through the apertures 160 in the base layer 132 into contact with the dressing bolster 114 and the epidermis 106. The adhesive 136 may be pressed through the apertures 160 in the base layer 132, for example, by applying pressure to an exterior surface of the sealing member 116. Pressure may be applied to the exterior surface of the sealing member 116 by hand, for example, to manipulate or force the adhesive 136 through the apertures 160 in the base layer 132. An aperture (not shown) may be formed or preformed in the sealing member 116 to provide fluid communication between the sealed space 119 and the reduced-pressure source 144, such as, for example, through the conduit interface 138 and the delivery conduit 148.

Reduced pressure may be applied to the tissue site 102, and fluid may be extracted from the tissue site 102 and into the dressing assembly 112. A portion of the fluid from the tissue site 102 may be absorbed into the interface seal 130. Further, the fluid from the tissue site 102 may be wicked or otherwise communicated in a lateral direction within the dressing assembly 112 toward the interface seal 130. The application of reduced pressure to the sealed space 119 may also contract the dressing bolster 114, imparting an inward force or an apposition force to the tissue site 102 that may move the first portion 172 of the tissue site 102 toward the second portion 174 of the tissue site 102. The movement of the first portion 172 toward or closer to the second portion 174 may provide closure of the incision 104 at the tissue site 102. The inward force or apposition force may be imparted to the tissue site 102 through the configuration of the base layer 132 and the interface seal 130 disclosed herein.

Figure 6:
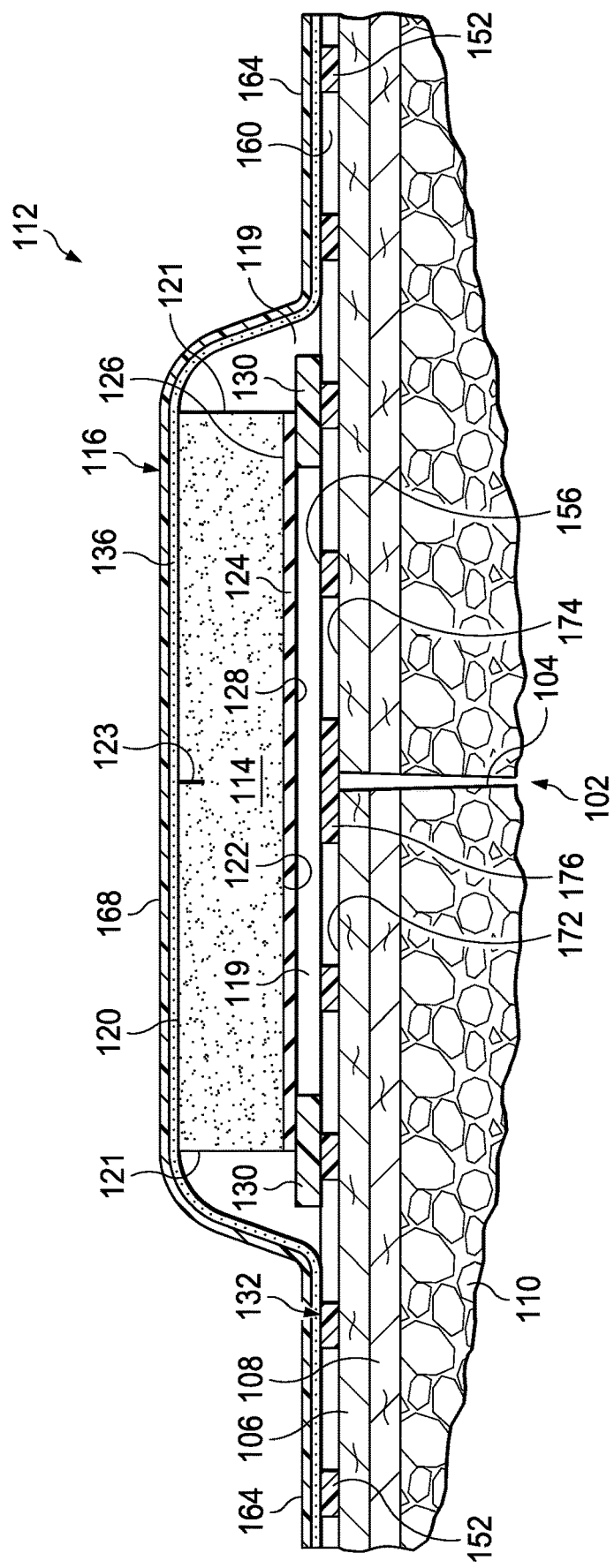
FIG. 6 is a perspective view of another illustrative embodiment of a system for treating a tissue site.

Referring to FIG. 6, in some embodiments, a portion of the base layer 132 may be configured to be positioned on or coupled to the second, inward-facing side 122 of the dressing bolster 114. For example, the central region 156 of the base layer 132 may be positioned on or coupled to the second, inward-facing side 122 of the dressing bolster 114. In some embodiments, the base layer 132 may be positioned between the dressing bolster 114 and the tissue site 102. Further, in some embodiments, the base layer 132 may be positioned or coupled relative to the dressing bolster 114 through other elements, such as, for example, the comfort layer 124 and/or the interface seal 130. For example, the comfort layer 124 may be positioned between the second, inward-facing side 122 of the dressing bolster 114 and the base layer 132. In other embodiments, the base layer 132 may be directly positioned on or directly coupled to the dressing bolster 114.

In some embodiments, the base layer 132 may include a bridge 176 configured to extend across or to cover a portion of the tissue site 102, such as, for example, the incision 104. In some embodiments, the bridge 176 may be configured to be positioned in direct contact with the incision 104, or other desired portion of the tissue site 102. In some embodiments, the bridge 176 may be a solid or continuous portion of the base layer 132 that is free of the apertures 160. Further, in some embodiments, the bridge 176 or other portion of the base layer 132 may be positioned in direct contact with scar tissue at the tissue site 102, or an area of the tissue site 102 prone to formation of scar tissue.

In some embodiments, the bridge 176 may be configured to extend between the first portion 172 of the tissue site 102 and the second portion 174 of the tissue site 102. The first portion 172 and the second portion 174 of the tissue site 102 may be, for example, on opposite sides of the incision 104, or other desired area of the tissue site 102.

In some illustrative embodiments, a method for treating the tissue site 102 may include providing the dressing bolster 114 having the first side 120, the second side 122, and the edge 121 defining the outer boundary of the dressing bolster 114. Further, the method may include positioning the interface seal 130 between the second side 122 of the dressing bolster 114 and the tissue site 102 at the edge 121 of the dressing bolster 114. Further, the method may include coupling the base layer 132 to the dressing bolster 114 and to a tissue, such as the epidermis 106, around the tissue site 102. Further, the method may include covering the first side 120 of the dressing bolster 114 with the sealing member 116 to form the sealed space 119 relative to the tissue site 102. The dressing bolster 114 may be positioned in the sealed space 119.

In some embodiments, the method may include positioning the second side 122 of the dressing bolster 114 facing the tissue site 102. Further, in some embodiments, the method may include positioning the comfort layer 124 between the second side 122 of the dressing bolster 114 and the interface seal 130. Further, in some embodiments, coupling the base layer 132 may include coupling the base layer 132 to a tissue around the edge 121 of the dressing bolster 114.

In some embodiments, at least a portion of the second side 122 of the dressing bolster 114 may be free of the interface seal 130 and positioned in fluid communication with the tissue site 102. Further, in some embodiments, the interface seal 130 may be positioned around the periphery 121 of the dressing bolster 114 and the tissue site 102. Further, in some embodiments, the interface seal 130 may substantially surround the periphery 121 of the dressing bolster 114 and the tissue site 102.

In some embodiments, the base layer 132 may include the plurality of apertures 160, and the step of coupling the base layer 132 may include positioning the adhesive 136 in fluid communication with a tissue around the tissue site 102 though the apertures 160 in the base layer 132. Further, in some embodiments, the method may include positioning the adhesive 136 between the sealing member 116 and the base layer 132. Further, in some embodiments, the method may include pressing the adhesive 136 through the plurality of apertures 160 in the base layer 132 into contact with a tissue around the tissue site 102. Further, in some embodiments, the base layer 132 may include the base layer flange 152 that may extend beyond the edge 121 of the dressing bolster 114 and into contact with a tissue around the tissue site 102. The plurality of apertures 160 may be disposed at least through the base layer flange 152.

In some embodiments, the method may include extracting fluid from the tissue site 102. Further, in some embodiments, the method may include drawing the first portion 172 of the tissue site 102 toward the second portion 174 of the tissue site 102. In some embodiments, drawing the first portion 172 of the tissue site 102 toward the second portion 174 of the tissue site 102 may include contracting the dressing bolster 114 by applying reduced pressure to the dressing bolster 114 and the sealed space 119. In some embodiments, contracting the dressing bolster 114 may impart an inward force between the first portion 172 of the tissue site 102 and the second portion 174 of the tissue site 102 through the interface seal 130 and the base layer 132.

Referring to FIG. 7, provided is a graph illustrating a plot of apposition force versus time for each of three dressings during intermittent application of reduced pressure at −125 mm Hg to each of the dressings. Two of the plots, designated as Baseline 1 and Baseline 2, illustrate the apposition force for each of two known or prior art dressings to establish two sets of baseline data for comparison. The third plot, designated as Improved Dressing Assembly, illustrates the apposition force for the dressing assembly 112 according to this disclosure, including the base layer 132 and the interface seal 130. As shown, the dressing assembly 112, including the base layer 132 and the interface seal 130, exhibited an increased apposition force at the tissue site compared to Baseline 1 and Baseline 2. Thus, the data shows that the disclosed configuration of the dressing assembly 112, including the base layer 132 and the interface seal 130, may provide an increase in the apposition force that may be imparted to a tissue site. Further, the use and configuration of the base layer 132 in the dressing assembly 112 as described herein may increase the temperature and hydration at the tissue site 102, which may be beneficial for reducing the formation of scar tissue, and the size and appearance of any existing scar tissue.

Although the subject matter of this disclosure has been provided by way of example in the context of certain illustrative, non-limiting embodiments, various changes, substitutions, permutations, and alterations can be made without departing from the scope of this disclosure as defined by the appended claims. Any feature described in connection to any one embodiment may also be applicable to any other embodiment. As such, the benefits and advantages described above may relate to one embodiment or may relate to several embodiments. Further, the steps of the methods described herein may be carried out in any suitable order, or simultaneously where appropriate.

We claim:

1. A system for treating a tissue site, comprising:
   a dressing bolster comprising a first side, a second side, and a periphery;
   a comfort layer comprising a first side and a second side, the first side of the comfort layer coupled to the second side of the dressing bolster, wherein a portion of the second side of the comfort layer is configured to directly contact the tissue site;
   an interface seal coupled to the second side of the comfort layer;
   a base layer comprising a base layer flange configured to be coupled to the dressing bolster and to extend beyond the periphery of the dressing bolster;
   a sealing member configured to cover the dressing bolster and to create a sealed space relative to the tissue site; and
   a reduced-pressure source configured to be coupled in fluid communication with the sealed space.

2. The system of claim 1, wherein the dressing bolster comprises foam.

3. The system of claim 1, wherein the comfort layer is selected from the group consisting of: a woven material; a non-woven material; a polyester knit material; and a fenestrated film.

4. The system of claim 1, wherein the interface seal comprises a hydrocolloid.

5. The system of claim 1, wherein the base layer comprises silicone.

6. The system of claim 1, wherein the sealing member comprises a liquid impermeable film.

7. The system of claim 1, wherein the comfort layer has a periphery substantially aligned with the periphery of the dressing bolster.

8. The system of claim 1, wherein a portion of the second side of the comfort layer is free of the interface seal.

9. The system of claim 1, wherein the periphery of the dressing bolster defines an outer boundary of the dressing bolster, and wherein the interface seal is positioned at the periphery of the dressing bolster.

10. The system of claim 1, wherein the interface seal extends beyond the periphery of the dressing bolster.

11. The system of claim 1, wherein a thickness of the interface seal relative to a thickness of the sealing member defines a ratio between about 2.7 to about 7.0.

12. The system of claim 1, wherein the base layer flange is configured to be positioned around the periphery of the dressing bolster.

13. The system of claim 1, wherein the base layer flange is configured to substantially surround the periphery of the dressing bolster.

14. The system of claim 1, wherein the base layer flange is configured to be coupled to a tissue around the tissue site.

15. The system of claim 1, wherein the base layer flange is configured to be positioned in direct contact with a tissue around the tissue site.

16. The system of claim 1, wherein the base layer includes a plurality of apertures disposed at least through the base layer flange, the system further comprising an adhesive positioned between the sealing member and the base layer such that the adhesive is in fluid communication with at least the apertures in the base layer flange.

17. The system of claim 1, wherein the base layer includes a plurality of apertures disposed at least through the base layer flange, the system further comprising an adhesive positioned between the sealing member and the base layer, the adhesive configured to be in fluid communication with a tissue around the tissue site through the apertures in the base layer flange.

18. The system of claim 1, wherein a portion of the base layer is configured to be directly coupled to the first side of the dressing bolster.

19. The system of claim 1, wherein a portion of the base layer is configured to be coupled to the second side of the dressing bolster.

20. The system of claim 1, wherein the base layer is configured to be positioned between the tissue site and the dressing bolster.

21. The system of claim 1, wherein the base layer further comprises a bridge configured to extend across an incision at the tissue site.

22. The system of claim 21, wherein the bridge is configured to be in direct contact with the incision.

23. The system of claim 1, wherein the base layer further comprises a bridge configured to extend between a first portion of the tissue site and a second portion of the tissue site.

24. The system of claim 1, wherein the interface seal is configured to be directly coupled to the second side of the comfort layer.

* * * * *